(12) United States Patent
Goodenowe

(10) Patent No.: US 10,302,624 B2
(45) Date of Patent: May 28, 2019

(54) METHODS FOR THE DIAGNOSIS AND RISK ASSESSMENT OF PLASMALOGEN DEFICIENCY MEDIATED DISEASES OF AGING

(71) Applicant: Med-Life Discoveries LP, Saskatoon (CA)

(72) Inventor: Dayan Goodenowe, Saskatoon (CA)

(73) Assignee: Med-Life Discoveries LP, Saskatoon, Saskatchewan (CA)

( * ) Notice: Subject to any disclaimer, the term of this patent is extended or adjusted under 35 U.S.C. 154(b) by 0 days.

(21) Appl. No.: 15/143,064

(22) Filed: Apr. 29, 2016

(65) Prior Publication Data

US 2016/0320366 A1    Nov. 3, 2016

Related U.S. Application Data

(63) Continuation of application No. 12/595,178, filed as application No. PCT/CA2008/000659 on Apr. 9, 2008, now abandoned.
(Continued)

(51) Int. Cl.
*G01N 33/92* (2006.01)
*G01N 33/49* (2006.01)
(Continued)

(52) U.S. Cl.
CPC ....... *G01N 33/49* (2013.01); *G01N 33/57484* (2013.01); *G01N 33/6896* (2013.01);
(Continued)

(58) Field of Classification Search
None
See application file for complete search history.

(56) References Cited

U.S. PATENT DOCUMENTS 5,631,168 A    5/1997 Growdon et al.
5,731,354 A    3/1998 Pruss
(Continued)

FOREIGN PATENT DOCUMENTS

WO    2001/61358 A1    8/2001
WO    2005/085838      9/2005
(Continued)

OTHER PUBLICATIONS

PCT International Search Report for PCT/CA2008/000659, dated Apr. 9, 2008.
(Continued)

*Primary Examiner* — Christopher Adam Hixson
*Assistant Examiner* — Michelle Adams
(74) *Attorney, Agent, or Firm* — Pepper Hamilton LLP

(57) ABSTRACT

The present invention relates to methods for the diagnosis and risk assessment of plasmalogen deficiency mediated diseases of aging. The present invention describes the relationship between plasmalogen biosynthesis dysfunction and the biochemical and clinical manifestations of age related disorders. Specifically the present invention describes an increased prevalence of colon cancer, prostate cancer, lung cancer, breast cancer, ovary cancer, kidney cancer, cognitive impairment and dementia in subjects suffering from adult onset plasmalogen biosynthesis disorder (AO-PBD).

19 Claims, 11 Drawing Sheets

Related U.S. Application Data

(60) Provisional application No. 60/911,548, filed on Apr. 13, 2007.

(51) Int. Cl.
  *G01N 33/574* (2006.01)
  *G01N 33/68* (2006.01)
  *H01J 49/00* (2006.01)
  *H01J 49/38* (2006.01)

(52) U.S. Cl.
  CPC .......... *G01N 33/92* (2013.01); *H01J 49/0031* (2013.01); *H01J 49/38* (2013.01); *G01N 2560/00* (2013.01); *G01N 2800/50* (2013.01); *G01N 2800/7042* (2013.01)

(56) References Cited

U.S. PATENT DOCUMENTS

| | | | |
|---|---|---|---|
| 6,177,476 B1 | 1/2001 | Peterson et al. | |
| 6,830,932 B1 | 12/2004 | Danne et al. | |
| 7,349,809 B2 | 3/2008 | Goodenowe | |
| 2008/0020472 A1* | 1/2008 | Shan | G01N 33/57449 436/64 |

FOREIGN PATENT DOCUMENTS

| | | |
|---|---|---|
| WO | 2007/061656 A2 | 5/2007 |
| WO | 2007/061940 A2 | 5/2007 |
| WO | 2007/098585 A1 | 9/2007 |

OTHER PUBLICATIONS

Goodenowe, et al. "Peripheral Ethanolamine Plasmalogen Deficiency: A Logical Causative Factor in Alzheimer's Disease and Dememtia," Journal of Lipid Research 48:2485-2498 (2007).

Nagan et al. "Plasmalogens: Biosynthesis and Functions," Prog Lipid Res. 40(3)199-229 (2001).

Yamazaki et al. "Serum Biomarker Panels Specific to Ad Pathology and Viability of Cholinergic Neurons," Presentation at the International College of Geriatric Psychoneuropharmacology Program P-C-16 (abstract), (2006).

Ginsberg et al., "Membrane Instability, Plasmalogen Content, and Alzheimer's Disease," J. Neurochem. 70 (6):2533-2538 (1998).

Gorgas et al., "The Ether Lipid-Deficient Mouse: Tracking Down Plasmalogen Functions," Biochimica et Biophysica Acta 1763:1511-1526 (2006).

Supplementary European Search Report dated Nov. 29, 2010 for corresponding application EP 08748108.

Ginsberg et al., "Disease and Anatomic Specificity of Ethanolamine Plasmalogen Deficiency in Alzheimer's Disease Brain," Brain Res. 698:223-226 (1995).

Maeba et al., "Plasmalogens in Human Serum Positively Correlate with High-Density Lipoprotein and Decrease with Aging," J. Atheroscl. Thromb. 14(1):12-18 (2007).

Perichon et al., "Peroxisomal Disease Cell Lines with Cellular Plasmalogen Deficiency have Impaired Muscarinic Cholinergic Signal Transduction Activity and Amyloid Precursor Protein Secretion," Biochem. Biophys. Res. Comm. 248:57-61 (1998).

Pettegrew et al., "Brain Membrane Phospholipid Alterations in Alzheimer's Disease," Neurochem. Res. 26(7):771-782 (2001).

Brites et al., "Functions and Biosynthesis of Plasmalogens in Health and Disease," Biochim. Biophys. Acta. 1636:219-231 (2004).

Sparks et al., "Statin Therapy in Alzheimer's Disease," Acta. Neural Scand. 114(Suppl. 185):78-86 (2006).

Behl et al., "Cholinesterase Inhibitors Slow Decline in Executive Functions, Rather than Memory, in Alzheimer's Disease: A 1-Year Observational Study in the Sunnybrook Dementia Cohort," Curr. Alz. Res. 3(2):147-156 (2006).

Alkan et al., "Delayed Myelination in a Rhizomelic Chondrodysplasia Punctata Case: MR Spectroscopy Findings," Mag. Res. Imag. 21:77-80 (2003).

Wanders, "Peroxisomal Disorders: Clinical, Biochemical, and Molecular Aspects," Neurochem. Res. 24(4):565-580 (1999).

Goldfischer et al., "Peroxisomal and Mitochondrial Defects in the Cerebro-Hepato-Renal Syndrome," Science 182 (107):62-64 (1973).

Bowen et al., "A Familial Syndrome of Multiple Congenital Defects," Bulletin of the Johns Hopkins Hospital 114:402-414 (1964).

van den Bosch et al., "Biochemistry of Peroxisomes," Annu. Rev. Biochem. 61:157-197 (1992).

Sztriha et al., "Abnormal Myelin Formation in Rhizomelic Chondrodysplasia Punctata Type 1 (DHAPAT-Deficiency)," Dev. Med. Child Neurol. 42:492-495 (2000).

de Duve, "The Peroxisome: A New Cytoplasmic Organelle," Proc. R. Soc. Land. B 173:71-83 (1969).

Conquer et al., "Fatty Acid Analysis of Blood Plasma of Patients with Alzheimer's Disease, Other Types of Dementia, and Cognitive Impairment," Lipids 35:1205-1312 (2000).

Han et al., "Plasmalogen Deficiency in Early Alzheimer's Disease Subjects and in Animal Models: Molecular Characterization Using Electrospray Ionization Mass Spectrometry," Journal of Neurochemistry, 77:1168-1180 (2001).

Mulder et al., "Decreased lysophosphatidylcholine/Phosphatidylcholine Ratio in Cerebrospinal Fluid in Alzheimer's Disease," Journal of Neural Transmission 110:949-955 (2003).

Lytle et al., "Utility of High Performance Liquid ChromatographylEledctrospray/Mass Spectrometry of Polar Lipids in Specifically Per-13C Labeled Gram-Negative Bacteria DA001 as a Tracer for Acceleration of Bioremediation in the Subsurface," Journal of Microbiological Methods 44: 271-281(2001).

Murphy et al., "Analysis of Nonvolatile Lipids by Mass Spectrometry," Chem. Rev. 101: 479-526 (2001).

Ujiie et al., "Blood-Brain Barrier Permeability Precedes Senile Plaque Formation in an Alzheimer Disease Model," Microcirculation 10:463-470 (2003).

Verken et al., "Analysis of Plasmenylethanolamines Using Electrospray Tandem Mass Spectrometry and It's Application in Screening for Peroxisomal Disorders," J. Inherit. Metab. Dis. 23:429-433 (2000).

Folch J., "A Simple Method for the Isolation and Purification of Total Lipides From Animal Tissues," J. Biol. Chem 226:497-506, (1957).

Zoeller et al., "Increasing Plasmalogen Levels Protects Human Endothelial Cells During Hypoxia," Am. J. Physiol. Heart. Circ. Physiol. 283(2):H671-9 (2002).

Nagan et al. "Plasmalogens: Biosynthesis and Functions," Progress in Lipid Research 40(3):199-229 (2001).

Martinez et al., "Therapeutic Effects of Docosahexaenoic Acid Ethyl Ester in Patients With Generalized Peroxisomal Disorders," Am. J. Clin. Nutr. 71(1 Suppl):376S-85S (2000).

Kuczynski et al., "Effects of Myo-Inositol Treatment on Plasmalogen Levels and Biosynthesis in Rat Brain," Proc. Intl. Soc. Mag. Reson. Med. 11:1966 (2003).

Martinez, "Restoring the DHA Levels in the Brains of Zellweger Patients," J. Mol. Neurosci. 16(2-3):309-16 (2001).

* cited by examiner

Log2[min((subject PlsEtn 16:0/18:2/PtdEtn 16:0/18:0)/(normal population PlsEtn 16:0/18:2/PtdEtn 16:0/18:0); (subject PlsEtn 16:0/22:6/PtdEtn 16:0/18:0)/(normal population PlsEtn 16:0/22:6/PtdEtn 16:0/18:0))]

Log2[min((subject PlsEtn 16:0/18:2/PtdEtn 16:0/18:0)/(normal population PlsEtn 16:0/18:2/PtdEtn 16:0/18:0); (subject PlsEtn 16:0/22:6/PtdEtn 16:0/18:0)/(normal population PlsEtn 16:0/22:6/PtdEtn 16:0/18:0))]

METHODS FOR THE DIAGNOSIS AND RISK ASSESSMENT OF PLASMALOGEN DEFICIENCY MEDIATED DISEASES OF AGING

CROSS-REFERENCE TO RELATED APPLICATIONS

This application is a continuation of U.S. patent application Ser. No. 12/595,178, which is a national stage application under 35 U.S.C. 371 of PCT/CA2008/000659, filed Apr. 9, 2008, and claims the priority benefit of U.S. Provisional Patent Application Ser. No. 60/911,548, filed Apr. 13, 2007.

FIELD OF INVENTION

The present invention relates to methods for the diagnosis of plasmalogen deficiency mediated diseases of aging. The present invention describes the relationship between plasmalogen biosynthesis dysfunction and the biochemical and clinical manifestations of age related disorders. Specifically the present invention describes an increased prevalence of colon cancer, prostate cancer, lung cancer, breast cancer, ovarian cancer, kidney cancer, cognitive impairment and dementia in subjects with decreased levels of plasmalogens.

BACKGROUND OF THE INVENTION

Accordingly, the present application describes the discovery of a late or adult onset form of peroxisomal dysfunction in humans. The disease manifests in subjects of all ages but the incidence increases with increasing age after age 50 and peaks in 60-69 year olds and decreases thereafter. Subjects suffering from age related plasmalogen deficiencies have abnormally low levels of circulating plasmalogens in their serum and an increased prevalence of colon cancer, prostate cancer, lung cancer, breast cancer, ovary cancer, kidney cancer, cognitive impairment and dementia relative to subjects without age related plasmalogen deficiencies.

The biosynthesis of plasmalogens has been recently reviewed in detail[1]. The first two steps in the plasmalogen biosynthesis pathway are carried out exclusively in peroxisomes (see FIGS. 1 and 22 for the full pathway). The free hydroxyl group of dihydroxyacetone phosphate (DHAP) is first acetylated by DHAP acyltransferase (DHAP-AT). The ether bond (plasmanyl) is then created by replacing the sn-1 acyl group with a fatty alcohol by alkyl-DHAP synthase. Loss of function of either of these two enzymes through point mutations, impaired peroxisomal targeting or due to general peroxisomal dysfunction results in a severe plasmalogen deficiency. The remaining key synthetic processes occur in the endoplasmic reticulum (ER) where the sn-2 position is acylated and phosphoethanolamine is added to the sn-3 position to create plasmanyl glycerophosphoethanolamine (GPE). The final step involves a plasmanyl-specific enzyme that desaturates the 1-O-alkyl ether to form the vinyl ether (plasmenyl) GPE species, commonly referred to as PlsEtn or plasmenylethanolamine, also commonly known as ethanolamine plasmalogens. All cells in the body are capable of synthesizing these molecules.

Peroxisomes were first discovered in the late 1960's by de Duve[2]. Since that time over 50 different biochemical pathways have been described to be performed by peroxisomes[3]. The nine primary biochemical systems are listed in Table 1. The first peroxisomal disease of humans (cerebro-hepato-renal syndrome of Zellweger) was clinically described in 1964 by Bowen et al[4]. In 1973, it was discovered that these patients had disturbed mitochondrial function and no functional peroxisomes[5]. Currently, there are seventeen human diseases that are characterized as peroxisomal in origin (reviewed by Wanders[6], Table 2). The peroxisomal disorders are not uniform. Different disorders present vastly different biochemical abnormalities with some of these abnormalities overlapping. Accordingly, the diseases can be characterized as being either a disorder of peroxisomal biogenesis in which there is a general, overall peroxisomal deficit or a disorder of a particular peroxisomal protein or enzyme system (Table 3).

Of the disorders currently characterized, only Rhizomelic Chondrodysplasia Punctata (RCDP) can be said to be caused by plasmalogen deficiency alone. The RDCP disorders are further grouped into type I, II, or III. All three RDCP types exhibit decreased levels of plasmalogens in the plasma and a decreased de novo synthesis capacity of plasmalogens in the liver. Peroxisomal function in these subjects is believed to be otherwise normal, except for decreased α-oxidation of phytanic acid in type I RCDP.

Subject suffering from RCDP exhibit severe mental retardation and dysplasias of the bone which result in stunted growth among other abnormalities. Subjects with RCDP show numerous neurological abnormalities, the most striking of which is delayed myelination[7,8], which is believed to be a direct result of decreased plasmalogen synthesis. Most subjects with RCDP do not live more than two years from birth.

Dysplasia is an abnormality in the appearance of cells indicative of an early step towards transformation into a neoplasia. Dysplasia is a pre-neoplastic state of a cell. This abnormal growth is restricted to the originating system or location, for example, a dysplasia in the epithelial layer will not invade into the deeper tissue, or a dysplasia solely in a red blood cell line (refractory anaemia) will stay within the bone marrow and cardiovascular systems. The best known form of dysplasia is the precursor lesions to cervical cancer, called cervical intraepithelial neoplasia (CIN). This lesion is usually caused by an infection with the human papilloma virus (HPV). Dysplasia of the cervix is almost always unsuspected by the woman. It is usually discovered by a screening test, the pap smear. The purpose of this test is to diagnose the disease early, while it is still in the dysplasia phase and easy to cure. Dysplasia is the earliest form of pre-cancerous lesion in which a cell begins to change away from its normal form to an abnormal, less differentiated form. Carcinoma in situ, meaning 'cancer in place', represents a final transformation of a dysplasic cell to cancer, though the cancer remains local and has not moved out of the original site. Dysplasia is not cancer.

Cancer is a state where the cells have lost their tissue identity and have reverted back to a primitive cell form that grows rapidly and without regulation. Invasive carcinoma is the final step in this sequence. It is a cancer which has invaded beyond the original tissue layer and is also able to spread to other parts of the body (metastasize), starting growth of the cancer there and destroying the affected organs. It can be treated, but not always successfully. However, if left untreated it is almost always fatal.

In summary, a selective deficiency in plasmalogen biosynthesis is known to result in the clinical manifestation of severe neurological and cellular growth abnormalities. Furthermore, the survival disadvantage of decreased plasmalogen biosynthesis is severe.

It is well known that many diverse human diseases such as cancer, dementia, or decreased cognitive functioning increase in incidence with age. From an epidemiological and statistical perspective, these diseases often look very similar. However, from a clinical perspective, each of the cancers, dementias, and decreased cognitive functioning are very different. Currently, the largest risk factor for these disorders is the subject's age. Furthermore, it is well established that most cancers, dementias, and decreased cognitive functioning have a long prodromal phase (5-15 years) in which the disease is present but at a sub-clinical manifestation. There are few, if any, practical methods to accurately and precisely identify subjects with a clearly elevated risk. Accordingly, there is a tremendous need to be able to accurately identify subsets of the general population subjects with biochemical abnormalities that are causally linked to the known biochemical etiology of chronic age-related disorders such as cancers, dementias and decreased cognitive functioning and then treat these subjects with safe and well tolerated therapeutics that can correct the biochemical abnormality and reduce the risk of disease occurrence in this sub-population.

Impaired membrane cholesterol regulation, membrane dynamics, muscarinic receptor signal transduction, and APP processing are implicated to various degrees and to various symptoms and pathologies observed in dementia and decreased cognitive functioning. The association of these biochemical systems and dementia are well established. Acetylcholinesterase (ACE) inhibitors act by increasing the retention time of ACh in the synaptic cleft and therefore increase muscarinic receptor transduction[9]. Statins act by reducing cholesterol levels[10]. Amyloid lowering drugs are currently in development and clinical trials for removing the accumulation or to reduce the production of amyloid plaques. Therefore, the direct findings presented above, strongly implicate plasmalogen biosynthesis impairment in the etiology of dementia and cognitive impairment. In applicant's co-pending application PCT/CA2007/000313, which is published as PCT Publication No. WO 2007/098585, metabolites selected from phosphatidlycholine-related compounds, ethanolamine plasmalogens, endogenous fatty acids, essential fatty acids, lipid oxidations byproducts, and metabolite derivatives of these metabolic classes were found to be at lower levels in samples from patients suffering from dementia. In the present invention a decrease in plasmalogens has been found in patients suffering from other age related diseases.

One of the defining features regarding cancer cells is that, unlike normal cells which rely almost entirely upon respiration for energy, cancer cells can utilize both respiration and glycolysis for energy. In cancer, much work is now focused on developing drugs that inhibit the glycolysis pathway. One of the defining features of aerobic glycolysis in cancer is an enhanced mitochondrial citrate export and the use of cytosolic citrate to form acetyl-CoA. Therefore, the direct findings presented above, that an impairment in plasmalogen biosynthesis result in both increased membrane cholesterol levels and increased cytosolic acetyl-CoA utilization, strongly implicate plasmalogen biosynthesis impairment in cancer etiology.

The present application describes a subset of adult humans (>age 40) who have abnormally low levels of plasmalogens in their serum. This deficiency has been determined to be due to decreased plasmalogen synthesis and not due to increased oxidative stress. Subjects with this disorder have an increased prevalence of cognitive impairment, dementia and cancer. The early diagnosis of these diseases, or the assessment of risk in subjects before they get these diseases will result in a tremendous improvement on the long-term quality of life of these subjects as well as have a tremendous long-term cost saving to existing health care systems.

SUMMARY OF THE INVENTION

The present invention relates to methods for the diagnosis of plasmalogen deficiency mediated diseases of aging. The present invention describes the relationship between plasmalogen biosynthesis dysfunction and the biochemical and clinical manifestations of age related disorders. Specifically the present invention describes an increased prevalence of colon cancer, prostate cancer, lung cancer, breast cancer, ovarian cancer, kidney cancer, cognitive impairment and dementia in subjects with decreased levels of plasmalogens.

The present invention discloses a novel method of diagnosing the presence of age-related plasmalogen deficiency in one or more than one subject by measuring the levels of one or more than one plasmenyl or plasmanyl ether lipid present in a serum sample taken from a subject of unknown disease status and comparing these levels to "normal" or age-related plasmalogen deficiency reference levels and through this comparison arriving at either an age-related plasmalogen deficiency positive or age-related plasmalogen deficiency negative diagnosis.

The present invention discloses a novel method of diagnosing the presence of age-related plasmalogen deficiency in one or more than one subject by comparing a mathematically determined plasmalogen score from the measurement of one or more than one plasmenyl or plasmanyl ether lipid present in a serum sample taken from one or more than one subject of unknown disease status and comparing this score to "normal" or age-related plasmalogen deficiency reference levels and through this comparison arriving at either an age-related plasmalogen deficiency positive or age-related plasmalogen deficiency negative diagnosis.

The present invention discloses a novel method of diagnosing the presence of age-related plasmalogen deficiency in one or more than one subject by comparing the ratio of one or more than one plasmenyl or plasmanyl ether lipid to one or more than one endogenous molecules unaffected or minimally affected by age-related plasmalogen deficiency from serum samples taken from one or more than one subject of unknown disease status and comparing these ratios to "normal" or age-related plasmalogen deficiency reference levels and through this comparison arriving at either an age-related plasmalogen deficiency positive or age-related plasmalogen deficiency negative diagnosis.

Since subjects with an age-related plasmalogen deficiency have elevated risk of getting cancer and dementia, the present invention discloses a novel method for identifying subjects that are at elevated risk of developing cancer or dementia. Accordingly, the present invention discloses a novel method of diagnosing an elevated risk of getting cancer or dementia in one or more than one subject by measuring the levels of one or more than one plasmenyl or plasmanyl ether lipid present in a serum sample taken from a subject of unknown disease status and comparing these levels to "normal" or age-related plasmalogen deficiency reference levels and through this comparison arriving at a determination of elevated risk or not.

Since subjects with an age-related plasmalogen deficiency have elevated risk of getting cancer and dementia, the present invention discloses a novel method for identifying subjects that are at elevated risk of developing cancer or dementia. Accordingly, the present invention discloses a novel method of diagnosing an elevated risk of getting cancer or dementia in one or more than one subject by comparing a mathematically determined plasmalogen score from the measurement of one or more than one plasmenyl or plasmanyl ether lipid present in a serum sample taken from one or more than one subject of unknown disease status and comparing this score to "normal" or age-related plasmalogen deficiency reference levels and through this comparison arriving at a determination of elevated risk or not.

Since subjects with an age-related plasmalogen deficiency have elevated risk of getting cancer and dementia, the present invention discloses a novel method of diagnosing an elevated risk of getting cancer or dementia in one or more than one subject by comparing the ratio of one or more than one plasmenyl or plasmanyl ether lipid to one or more than one endogenous molecules unaffected or minimally affected by age-related plasmalogen deficiency from serum samples taken from one or more than one subject of unknown disease status and comparing these ratios to "normal" or age-related plasmalogen deficiency reference levels and through this comparison arriving at a determination of elevated risk or not.

Since there is an increased prevalence of an age-related plasmalogen deficiency in subjects currently suffering from cancer or dementia, the present invention discloses a novel method for identifying subjects with undiagnosed cancer or dementia. Accordingly, the present invention discloses a novel method of identifying undiagnosed cancer or dementia in one or more than one subject by measuring the levels of one or more than one plasmenyl or plasmanyl ether lipid present in a serum sample taken from a subject of unknown disease status and comparing these levels to "normal" or age-related plasmalogen deficiency reference levels. Subjects that test positive for an age-related plasmalogen deficiency are then tested by conventional cancer and dementia diagnostic methods to determine the location of the cancer and/or the severity and type of dementia present in said subject.

Since there is an increased prevalence of an age-related plasmalogen deficiency in subjects currently suffering from cancer or dementia, the present invention discloses a novel method for identifying subjects with undiagnosed cancer or dementia. Accordingly, the present invention discloses a novel method of identifying undiagnosed cancer or dementia in one or more than one subject by comparing a mathematically determined plasmalogen score from the measurement of one or more than one plasmenyl or plasmanyl ether lipid present in a serum sample taken from one or more than one subject of unknown disease status and comparing this score to "normal" or age-related plasmalogen deficiency reference levels. Subjects that test positive for an age-related plasmalogen deficiency are then tested by conventional cancer and dementia diagnostic methods to determine the location of the cancer and/or the severity and type of dementia present in said subject.

Since there is an increased prevalence of an age-related plasmalogen deficiency in subjects currently suffering from cancer or dementia, the present invention discloses a novel method for identifying subjects with undiagnosed cancer or dementia. Accordingly, the present invention discloses a novel method of identifying undiagnosed cancer or dementia in one or more than one subject by comparing the ratio of one or more than one plasmenyl or plasmanyl ether lipid to one or more than one endogenous molecules unaffected or minimally affected by age-related plasmalogen deficiency from serum samples taken from one or more than one subject of unknown disease status and comparing these ratios to "normal" or age-related plasmalogen deficiency reference levels. Subjects that test positive for age-related plasmalogen deficiency are then tested by conventional cancer and dementia diagnostic methods to determine the location of the cancer and/or the severity and type of dementia present in said subject.

The present invention provides a method for identifying an individual who would benefit from an age-related plasmalogen deficiency-targeted therapy comprising: analyzing a blood sample from a test subject to obtain quantifying data on all or a subset of the metabolites listed in Table 5, or closely related entities; comparing the data obtained on said metabolites in said test subject with reference data obtained from the analysis of a plurality of age-related plasmalogen deficiency humans or from a plurality of non-age-related plasmalogen deficiency humans; and using said comparison to determine the probability that the test subject would benefit from an age-related plasmalogen deficiency-targeted therapy.

The present invention provides a method for monitoring the effect of an age-related plasmalogen deficiency-targeted therapy comprising: analyzing a plurality of blood samples from a test subject prior to the initiation, during administration, or following administration of such therapy to obtain quantifying data on all or a subset of the metabolites listed in Table 5, or closely related entities; comparing the data obtained on said metabolites in said samples to each other or to reference data obtained from the analysis of a plurality of age-related plasmalogen deficiency humans or from a plurality of non-age-related plasmalogen deficiency humans; and using said comparison to determine the probability that the test subject would benefit from the continued treatment of an age-related plasmalogen deficiency-targeted therapy.

The impact of the present invention on the diagnosis of age-related plasmalogen deficiency and diseases caused by age-related plasmalogen deficiency would be tremendous, as literally everyone could be screened longitudinally throughout their lifetime to assess risk.

Given that the causal relationship between age-related plasmalogen deficiency and cancer and dementia is stronger than any previously described relationship and that the performance characteristics of the methods described in the present invention are representative for the general population, these methods alone may be superior to any other currently available screening method for cancer, dementia and cognitive impairment, as it may have the potential to detect disease progression prior to the emergence of clinical symptoms allowing for earlier intervention and subsequent better prognosis for subjects suffering from these diseases.

This summary of the invention does not necessarily describe all features of the invention.

BRIEF DESCRIPTION OF THE DRAWINGS

These and other features of the invention will become more apparent from the following description in which reference is made to the appended drawings wherein:

(FIG. 15A) Mono and di-unsaturated PlsEtn. (FIG. 15B) Polyunsaturated PlsEtn and free DHA (22:6). PlsEtn abbreviations: (fatty acid carbons: double bonds, not including the vinyl ether double bond) and position on glycerol backbone (sn-1/sn-2). 22:6 represents free DHA. Values are expressed as mean±SEM (n=19-112). CN refers to "Cognitive Normal".

DETAILED DESCRIPTION

Figure 1:
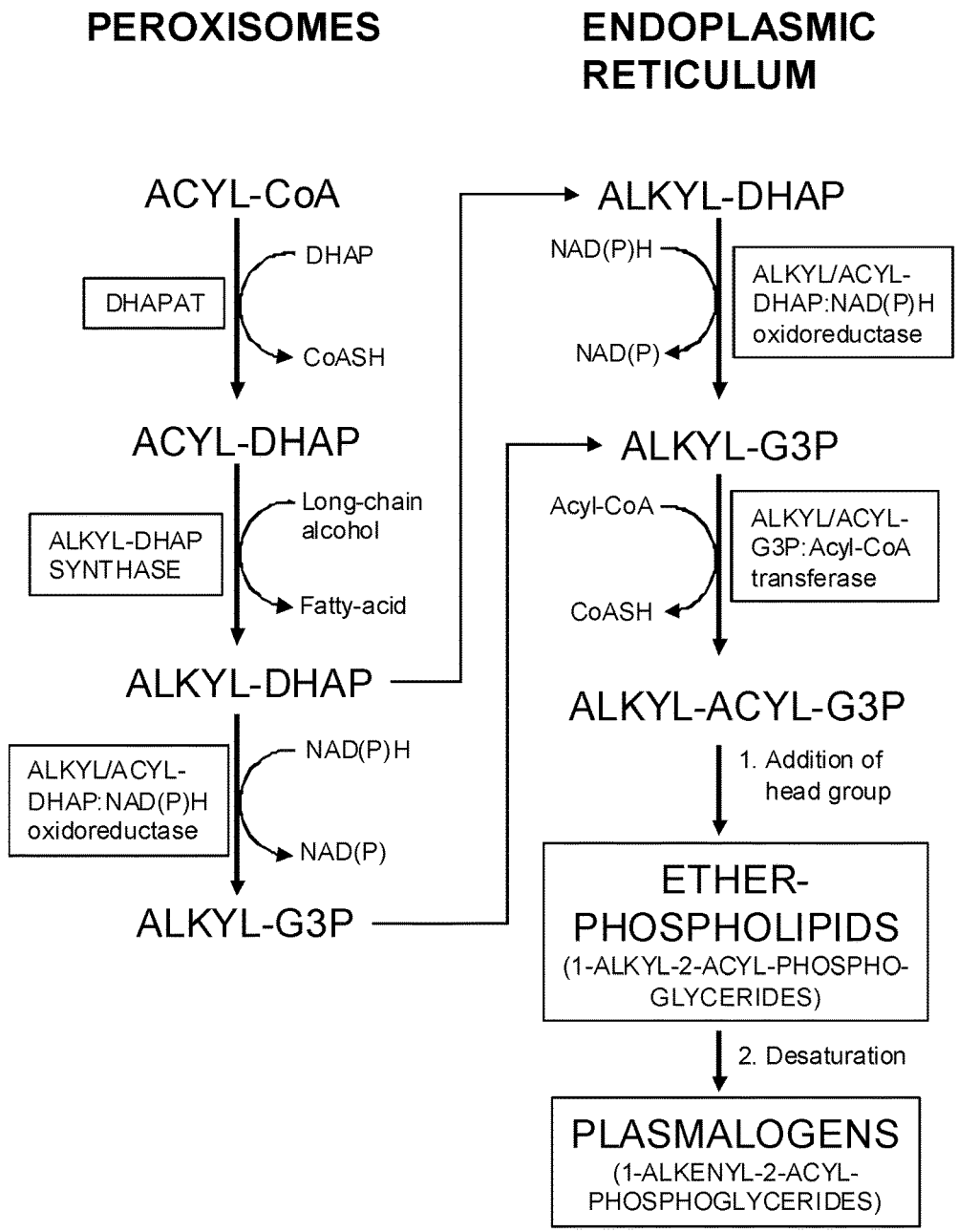
FIG. 1 shows the biosynthesis pathway for plasmalogens.

The present invention relates to methods for the diagnosis of plasmalogen deficiency mediated diseases of aging. The present invention describes the relationship between plasmalogen biosynthesis dysfunction and the biochemical and clinical manifestations of age related disorders. Specifically the present invention describes an increased prevalence of colon cancer, prostate cancer, lung cancer, breast cancer, ovarian cancer, kidney cancer, cognitive impairment and dementia in subjects with decreased levels of plasmalogens.

Accordingly, the present invention describes the discovery of a late or adult onset form of peroxisomal dysfunction in humans. The disease manifests in subjects of all ages but the incidence increases with increasing age after age 50 and peaks in 60-69 year olds and decreases thereafter. Subjects suffering from age related plasmalogen deficiencies have abnormally low levels of circulating plasmalogens in their serum and an increased prevalence of colon cancer, prostate cancer, lung cancer, breast cancer, ovary cancer, kidney cancer, cognitive impairment and dementia relative to subjects without age related plasmalogen deficiencies. The terms age-related plasmalogen deficiency or adult onset plasmalogen biosysnthesis disorder, or AO-PBD have been used throughout this application to describe this disorder. Although the embodiments of this invention have been exemplified for increase prevalence of colon cancer, prostate cancer, lung cancer, breast cancer, ovary cancer, kidney cancer, cognitive impairment or dementia, other age-related plasmalogen deficiency disorders can be diagnosed, or the risk of acquiring said disorders can be assessed according to the present invention.

The diagnostic method of the present invention is minimally invasive and is indicative of AO-PBD. Translation of the method into a clinical assay compatible with current clinical chemistry laboratory hardware is commercially acceptable and effective. Furthermore, the method of the present invention does not require highly trained personnel to perform and interpret the test.

The biological samples could originate from anywhere within the body, for example but not limited to, blood (serum/plasma), cerebral spinal fluid (CSF), urine, stool, breath, saliva, or biopsy of any solid tissue including tumor, adjacent normal, smooth and skeletal muscle, adipose tissue, liver, skin, hair, brain, kidney, pancreas, lung, colon, stomach, or other. Of particular interest are samples that are serum or CSF. While the term "serum" is used herein, those skilled in the art will recognize that plasma or whole blood or a sub-fraction of whole blood may be used.

When a blood sample is drawn from a patient there are several ways in which the sample can be processed. The range of processing can be as little as none (i.e. frozen whole blood) or as complex as the isolation of a particular cell type. The most common and routine procedures involve the preparation of either serum or plasma from whole blood. All blood sample processing methods, including spotting of blood samples onto solid-phase supports, such as filter paper or other immobile materials, are also contemplated by the invention.

The processed blood sample described above is then further processed to make it compatible with the methodical analysis technique to be employed in the detection and measurement of the biochemicals contained within the processed serum sample. The types of processing can range from as little as no further processing to as complex as differential extraction and chemical derivatization. Extraction methods could include sonication, soxhlet extraction, microwave assisted extraction (MAE), supercritical fluid extraction (SFE), accelerated solvent extraction (ASE), pressurized liquid extraction (PLE), pressurized hot water extraction (PHWE) and/or surfactant assisted extraction (PHWE) in common solvents such as methanol, ethanol, mixtures of alcohols and water, or organic solvents such as ethyl acetate or hexane. The preferred method of extracting metabolites for HTS analysis is to perform a liquid/liquid extraction whereby non-polar metabolites dissolve in an organic solvent and polar metabolites dissolve in an aqueous solvent.

One embodiment of the present invention detects and measures a panel of metabolites in which a subset were found to have statistically significantly differential abundances between AO-PBD and normal serum. In one embodiment the panel of metabolites is one or more than one metabolites listed in Table 5.

The present invention provides a method for diagnosing AO-PBD or the risk of AO-PBD in a patient, the method comprising the steps of:
  a) analyzing a sample from said patient to obtain quantifying data for one or more than one metabolite marker;
  b) comparing the quantifying data for said one or more than one metabolite marker to corresponding data obtained from one or more than one reference sample, wherein said comparison can be used to diagnose AO-PBD or the risk of AO-PBD.

The step of analyzing the sample may comprise analyzing the sample using a mass spectrometer (MS). For example, and without wishing to be limiting, such mass spectrometer could be of the FTMS, orbitrap, time of flight (TOF) or quadrupole types. Alternatively, the mass spectrometer could be equipped with an additional pre-detector mass filter. For example, and without wishing to be limiting such instruments are commonly referred to as quadrupole-FTMS (Q-FTMS), quadrupole-TOF (Q-TOF) or triple quadrupole (TQ or QQQ). In addition, the mass spectrometer could be operated in either the parent ion detection mode (MS) or in MSn mode, where n>=2. MSn refers to the situation where the parent ion is fragmented by collision induced dissociation (CID) or other fragmentation procedures to create fragment ions, and then one or more than one of said fragments are detected by the mass spectrometer. Such fragments can then be further fragmented to create further fragments. Alternatively, the sample could be introduced into the mass spectrometer using a liquid or gas chromatographic system or by direct injection.

The extracted samples may be analyzed using any suitable method know in the art. For example, and without wishing to be limiting in any manner, extracts of biological samples are amenable to analysis on essentially any mass spectrometry platform, either by direct injection or following chromatographic separation. Typical mass spectrometers are comprised of a source which ionizes molecules within the sample, and a detector for detecting the ionized molecules or fragments of molecules. Non-limiting examples of common sources include electron impact, electrospray ionization (ESI), atmospheric pressure chemical ionization (APCI), atmospheric pressure photo ionization (APPI), matrix assisted laser desorption ionization (MALDI), surface enhanced laser desorption ionization (SELDI), and derivations thereof. Common mass separation and detection systems can include quadrupole, quadrupole ion trap, linear ion trap, time-of-flight (TOF), magnetic sector, ion cyclotron (FTMS), Orbitrap, and derivations and combinations thereof. The advantage of FTMS over other MS-based platforms is its high resolving capability that allows for the separation of metabolites differing by only hundredths of a Dalton, many which would be missed by lower resolution instruments.

By the term "metabolite", it is meant specific small molecules, the levels or intensities of which are measured in a sample, and that may be used as markers to diagnose a disease state. These small molecules may also be referred to herein as "metabolite marker", "metabolite component", "biomarker", or "biochemical marker".

The metabolites are generally characterized by their accurate mass, as measured by mass spectormetry technique used in the above method. The accurate mass may also be referred to as "accurate neutral mass" or "neutral mass". The accurate mass of a metabolite is given herein in Daltons (Da), or a mass substantially equivalent thereto. By "substantially equivalent thereto", it is meant that a +/−5 ppm difference in the accurate mass would indicate the same metabolite, as would be recognized by a person of skill in the art. The accurate mass is given as the mass of the neutral metabolite. As would be recognized by a person of skill in the art, the ionization of the metabolites, which occurs during analysis of the sample, the metabolite will cause either a loss or gain of one or more hydrogen atoms and a loss or gain of an electron. This changes the accurate mass to the "ionized mass", which differs from the accurate mass by the mass of hydrogens (or other adducts such as sodium, potassium, ammonia, and others known in the art) and electrons lost or gained during ionization. Unless otherwise specified, the accurate neutral mass will be referred to herein.

Similarly, when a metabolite is described by its molecular formula the molecular formula of the neutral metabolite will be given. Naturally, the molecular formula of the ionized metabolite will differ from the neutral molecular formula by the number of hydrogens (or other adducts such as sodium, potassium, ammonia, and others known in the art) lost or gained during ionization.

Data is collected during analysis and quantifying data for one or more than one metabolite is obtained. "Quantifying data" is obtained by measuring the levels or intensities of specific metabolites present in a sample.

The quantifying data is compared to corresponding data from one or more than one reference sample. The "reference sample" is any suitable reference sample for the particular disease state. For example, and without wishing to be limiting in any manner, in the present invention the reference sample may be a sample from a non-AO-PBD control individual, i.e., a person not suffering from any age-related plasmalogen deficiency disease (also refered to herein as a "'normal' counterpart"). As would be understood by a person of skill in the art, more than one reference sample may be used for comparison to the quantifying data.

In yet another embodiment of the present invention, there is provided a method for diagnosing AO-PBD or the risk of AO-PBD in a patient. The method comprising the steps of:
  a) analyzing a sample from said patient to obtain quantifying data for one or more than one metabolite marker;
  b) obtaining a ratio for each of the one or more than one metabolite marker to an internal control metabolite;
  c) comparing each ratio of said one or more than one metabolite marker to the internal control metabolite to corresponding data obtained from one or more than one reference sample, wherein said comparison can be used to diagnose AO-PBD or the risk of AO-PBD.

The step of analyzing the sample can be as described above. The one or more than one reference sample may be a first reference sample obtained from a non-AO-PBD control individual. The "internal control metabolite" refers to an endogenous metabolite naturally present in the patient. Any suitable endogenous metabolite that does not vary over the disease states can be used as the internal control metabolite. For example, and without wishing to be limiting, the internal control metabolite may be phosphatidylethanolamine 16:0/18:0 (PtdEtn 16:0/18:0, M01), as shown in Table 5; this internal control metabolite has a molecular formula of $C_{39}H_{78}NO_8P$, and a structure characterized as

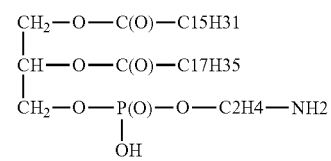

Use of the ratio of the metabolite marker to the internal control metabolite offers measurement that are more stable and reproducible than measurement of absolute levels of the metabolite marker. As the internal control metabolite is naturally present in all samples and does not appear to vary significantly over disease states, the sample-to-sample variability (due to handling, extraction, etc) is minimized.

The molecules described in the invention are listed in Table 5. This selection of molecules represents a representative sampling of diacyl, plasmanyl, and plasmenyl GPEs. However, someone skilled in the art would recognize that other molecules of similar structure which are involved in similar biochemical pathways could be used for similar purposes as described below. All such modifications of the invention are contemplated herein.

The present invention also provides high throughput methods for diagnosis of AO-PBD. The method involves fragmentation of the parent molecule; in a non-limiting example, this may be accomplished by a Q-Trap™ system. Detection of the metabolites may be performed using one of various assay platforms, including colorimetric chemical assays (UV, or other wavelength), antibody-based enzyme-linked immunosorbant assays (ELISAs), chip-based and polymerase-chain reaction for nucleic acid detection assays, bead-based nucleic-acid detection methods, dipstick chemical assays or other chemical reaction, image analysis such as magnetic resonance imaging (MRI), positron emission tomography (PET) scan, computerized tomography (CT) scan, nuclear magnetic resonance (NMR), and various mass spectrometry-based systems. The preferred method is a high throughput screening assay.

Figure 23:
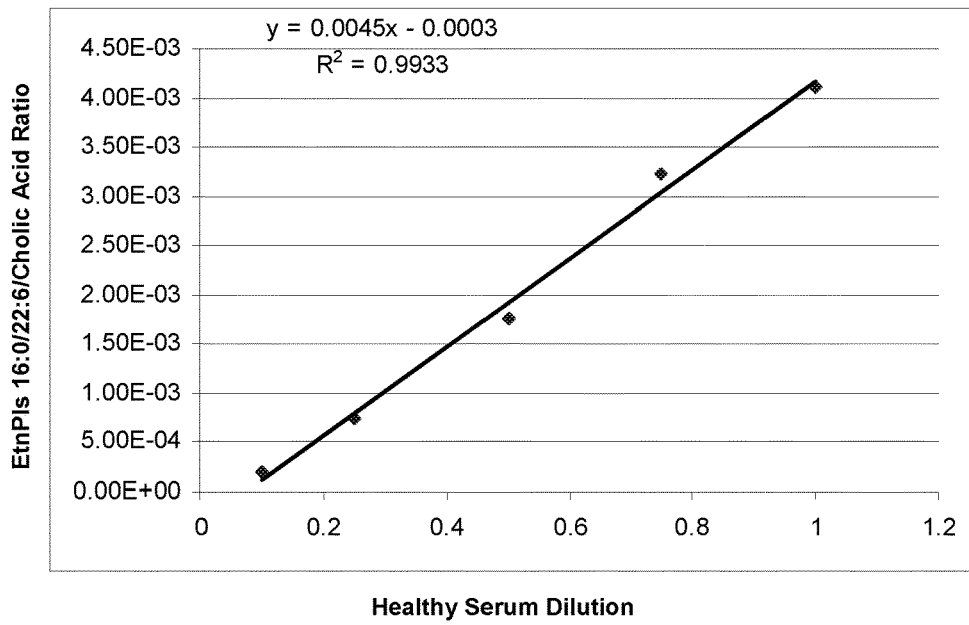
FIG. 23 shows the Q-Trap flow injection analysis standard curve of PlsEtn 16:0/22:6 in healthy human serum.

High throughput screening (HTS) was performed with a linear ion trap mass spectrometer (Q-trap 4000, Applied Biosystem) coupled with Agilent 1100 LC system. Sample was prepared by adding 15 uL of internal standard (5 µg/mL of (24-13C)-Cholic Acid in methanol) to 120 uL ethyl acetate fraction of each sample. 100 ul sample was injected by flow injection analysis (FIA), and monitored under negative APCI mode. The method was based on multiple reaction monitoring (MRM) scan mode of one parent/daughter transition for each metabolite and one internal standard. Each transition was scanned for 70 ms for a total cycle time of 2.475 sec. The isocratic 10% EtOAc in MeOH elution was performed with a flow rate at 360 µl/min for 1 min. The source parameters were set as follows: CUR: 10.0, CAD: 8, NC: −4.0, TEM: 400, GS1: 30, GS2: 50, interface heater on. The compound parameters were set as follows: DP: −120.0, EP: −10, NC: −4.0, CE: −40, CXP: −15. FIG. 23 illustrates a representative standard curve for this method for PlsEtn 16:0/22:6 generated by diluting a normal serum sample while maintaining a constant concentration of internal standard (24-13C)-Cholic Acid).

According to the present invention, there is a diagnostic relationship between decreased plasmalogens and cancer and/or dementia. Since subjects with an age-related palsmalogen deficiency have an elevated risk of developing cancer or dementia, this invention also provides a method of diagnosing an elevated risk of getting cancer or dementia in a subject by measuring the levels of one or more than one plasmenyl or plasmanyl ether lipid present in a serum sample taken from a subject of unknown disease status and comparing the levels to "normal" or age-related deficiency reference levels and through this comparison arriving at a determination of elevated risk or not. The samples and the diagnostic methods according to this aspect of the invention are as described in detail above.

Since there is an increased prevalence of an age-related plasmalogen deficiency in subjects currently suffering from cancer or dementia, the present invention also discloses a novel method for identifying subjects with undiagnosed cancer or dementia. Accordingly, the present invention discloses a novel method of identifying undiagnosed cancer or dementia in one or more than one subject by measuring the levels of one or more than one plasmenyl or plasmanyl ether lipid present in a serum sample taken from a subject of unknown disease status and comparing these levels to "normal" or age-related plasmalogen deficiency reference levels. The samples and the diagnostic methods according to this aspect of the invention are as described in detail above. Subjects that test positive for an age-related plasmalogen deficiency are then tested by conventional cancer and dementia diagnostic methods to determine the location of the cancer and/or the severity and type of dementia present in said subject.

The utility of the present invention will be further illustrated using the following examples.

EXAMPLES

Example 1

Characterization of AO-PBD as a Separate and Distinct Disease State

In order to determine if AO-PBD is truly a separate disease state or merely a symptom of a previously characterized human disease we executed the following experiments:

Co-Morbidity Analysis

Figure 2:
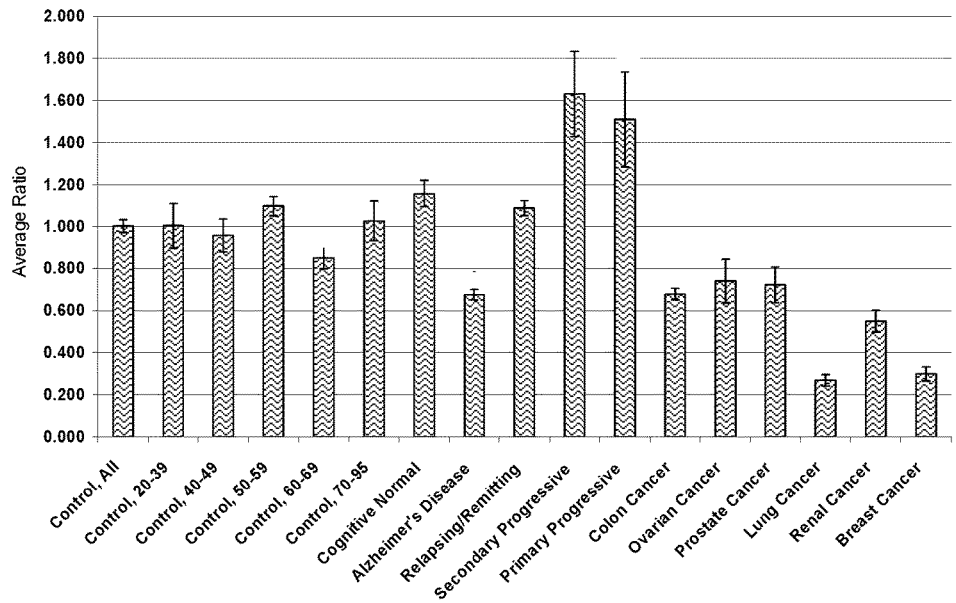
FIG. 2 shows the average ratio of plasmenyl 16:0/22:6 to diacyl 16:0/18:0 across different diseases.
Figure 3:
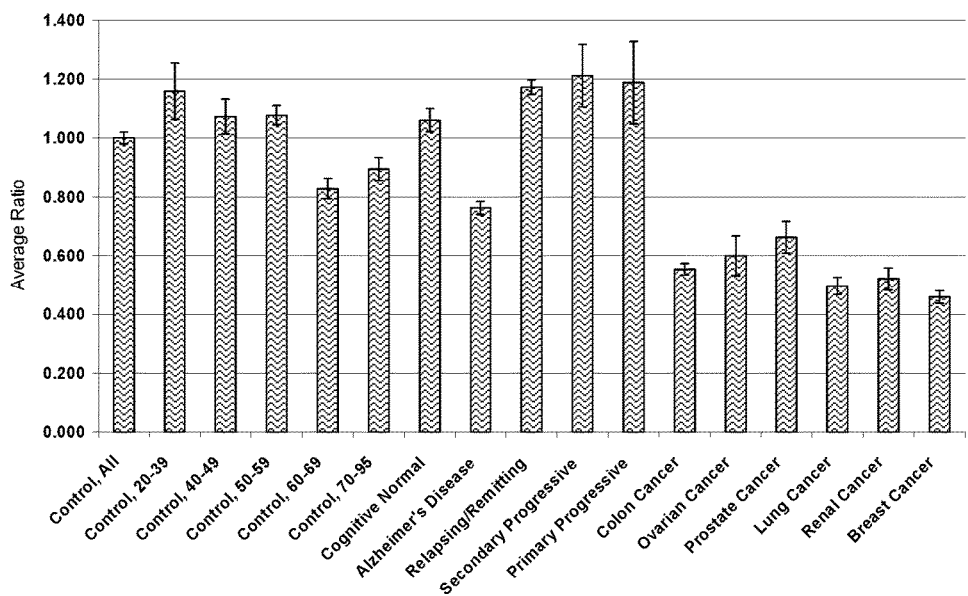
FIG. 3 shows the average ratio of plasmenyl 16:0/18:2 to diacyl 16:0/18:0 across different diseases.

Since the symptoms of RCDP implicate both cancer and neurological disease, we investigated the levels of various GPEs in lung, breast, colon, prostate, ovarian, and to renal cancers, the three types of multiple sclerosis (relapsing remitting, secondary progressive, and primary progressive), probable dementia of the Alzheimer's type, and in pathologically confirmed Alzheimer's. The serum levels of four diacyl, eight plasmanyl, and eight plasmenyl GPEs and free DHA and arachadonic acid were analyzed in 1369 subjects of various ages and diseases (Tables 4 and 5). Tables 6 to 11 show the results for each of the molecules studied. FIGS. 2 and 3 display the average and SEM of two prototypical plasmenyl GPEs (16:0/18:2 and 16:0/22:6 respectively). Plasmenyl 16:0/18:2 is a prototypical white matter plasmalogen containing a simple di-unsaturated fatty acid at sn-2 (linoleic acid) and plasmenyl 16:0/22:6 is a prototypical gray matter plasmalogen containing a polyunsaturated fatty acid at sn-2 (DHA). Each molecule is expressed as the ratio to the diacyl GPE 16:0/18:0 and further normalized to the mean control population ratio for ease of viewing. Plasmenyl 16:0/18:2 and 16:0/22:6 are significantly lower in all of the cancers and in probable Alzheimer's, but not in any of the multiple sclerosis groups. In fact, plasmenyl 16:0/22:6 is actually statistically elevated in secondary progressive and primary progressive MS. The other important observation from these two graphs is that there is a significant decrease in plasmalogens in the age 60-69 age group versus the age 50-59 group.

Figure 4:
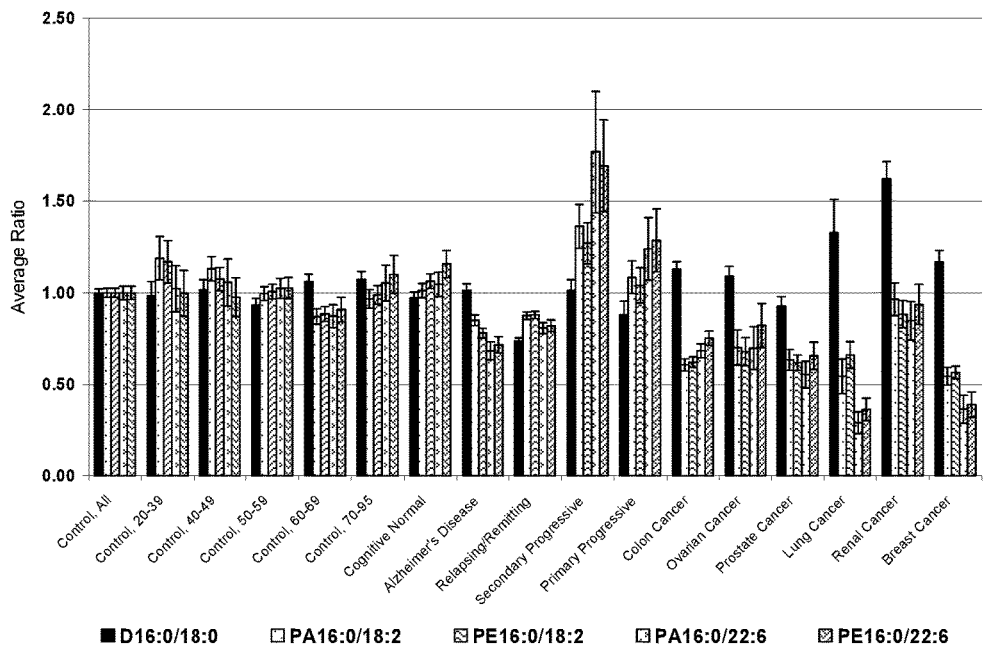
FIG. 4 shows the mean+/−SEM of diacyl 16:0/18:0 (M01), plasmanyl 16:0/18:2 (M11), plasmenyl 16:0/18:2 (M16), plasmanyl 16:0/22:6 (M09), and plasmenyl 16:0/22:6 (M19) (SEM: Standard Error of the Mean).
Figure 5:
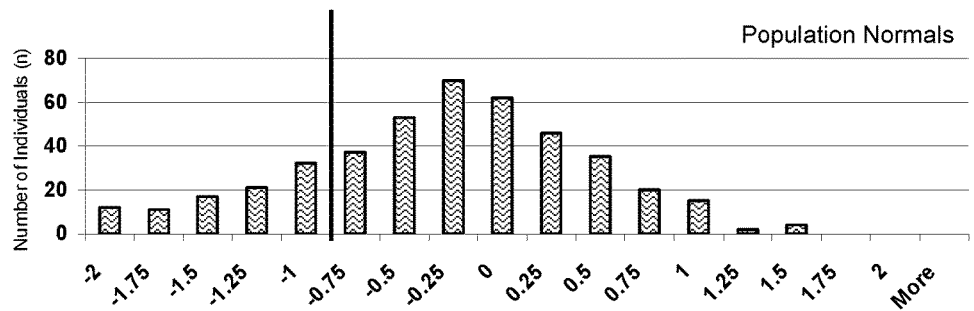
FIG. 5 shows the distribution of plasmalogen concentrations in population normals.
Figure 6:
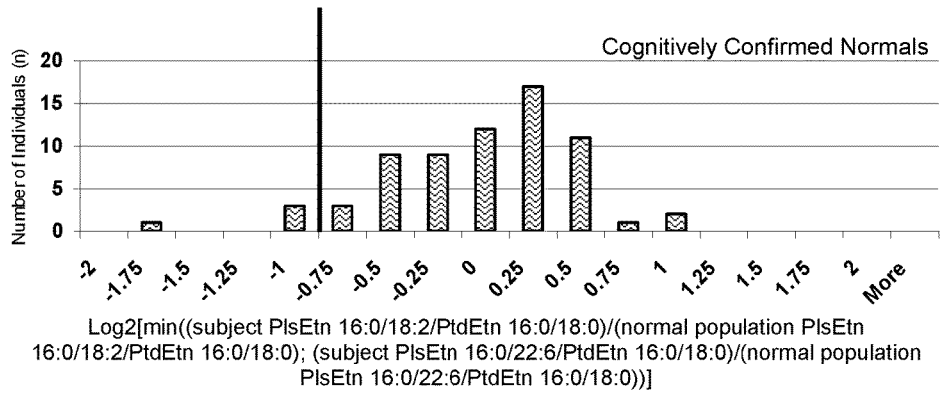
FIG. 6 shows the distribution of plasmalogen concentrations in cognitive confirmed normals.
Figure 7:
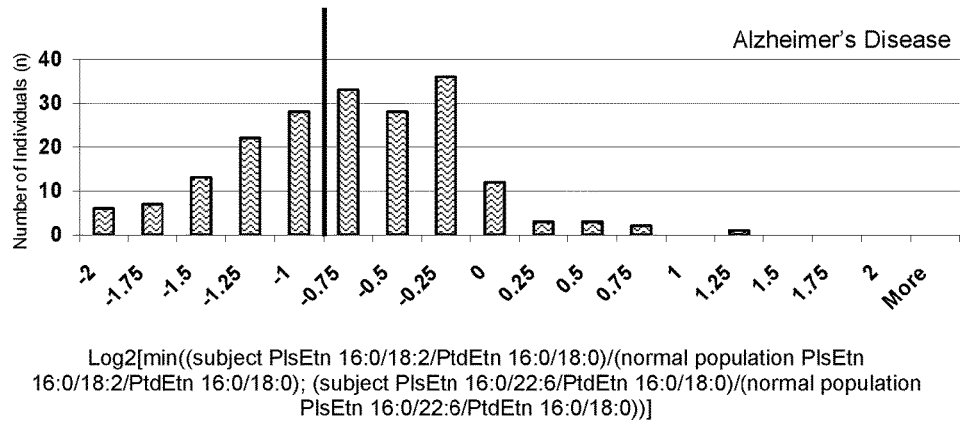
FIG. 7 shows the distribution of plasmalogen concentrations in probable AD patients.
Figure 8:
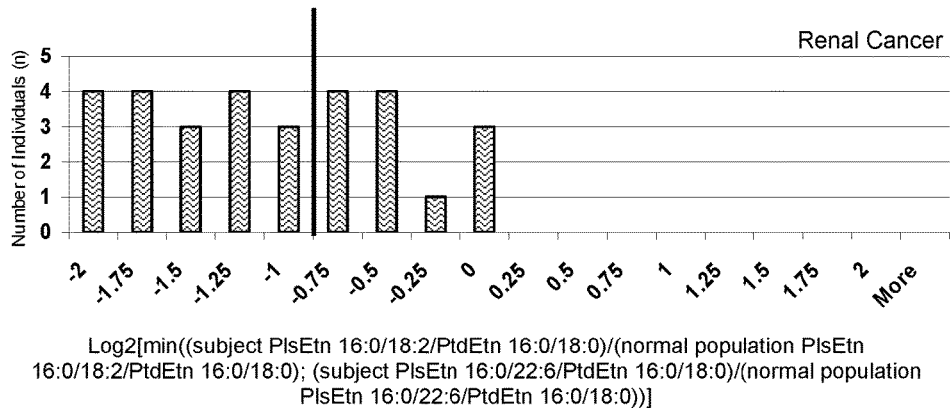
FIG. 8 shows the distribution of plasmalogen concentrations in renal cancer patients.
Figure 9:
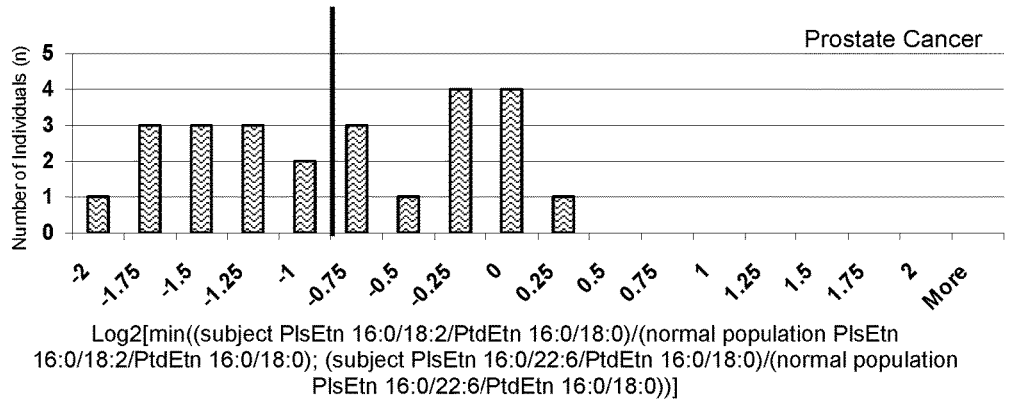
FIG. 9 shows the distribution of plasmalogen concentrations in prostate cancer patients.
Figure 10:
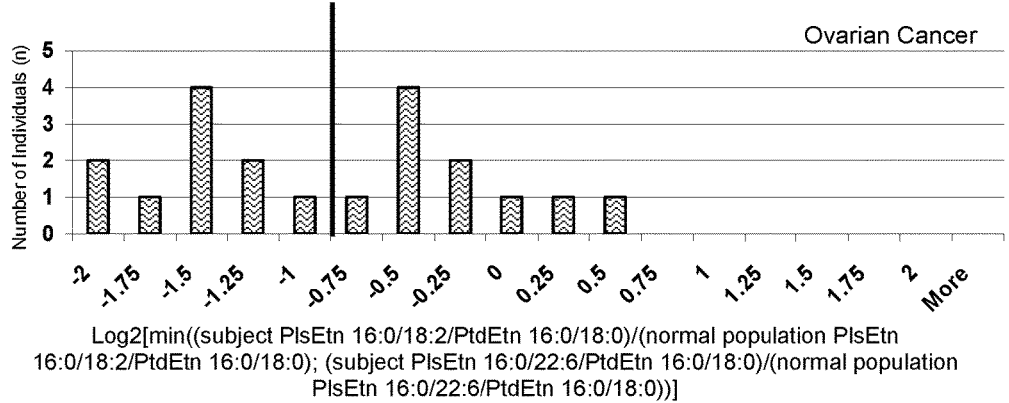
FIG. 10 shows the distribution of plasmalogen concentrations in ovarian cancer patients.
Figure 11:
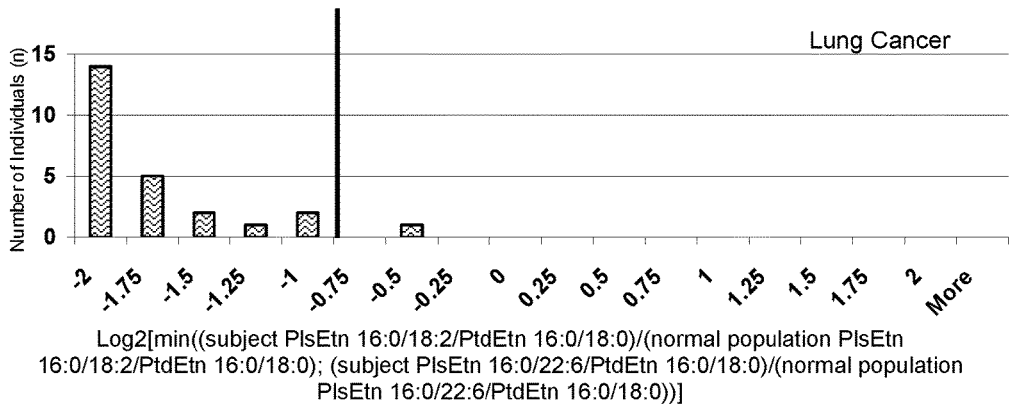
FIG. 11 shows the distribution of plasmalogen concentrations in lung cancer patients.
Figure 12:
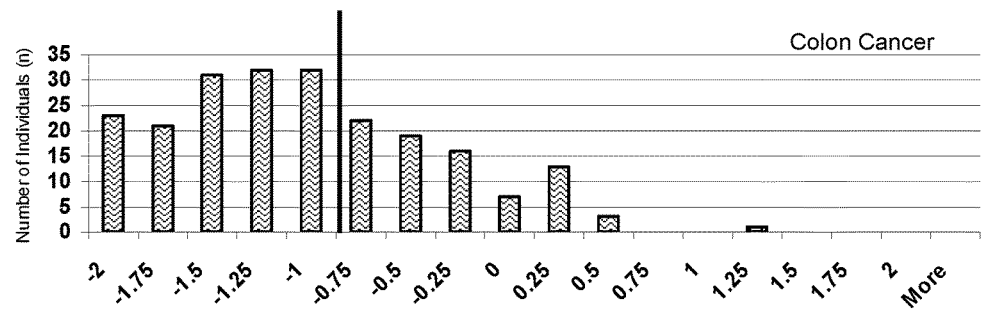
FIG. 12 shows the distribution of plasmalogen concentrations in colon cancer patients.
Figure 13:
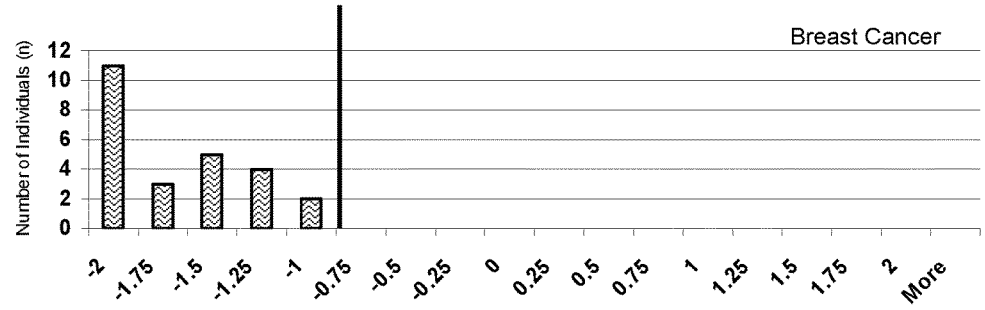
FIG. 13 shows the distribution of plasmalogen concentrations in breast cancer patients.
Figure 22:
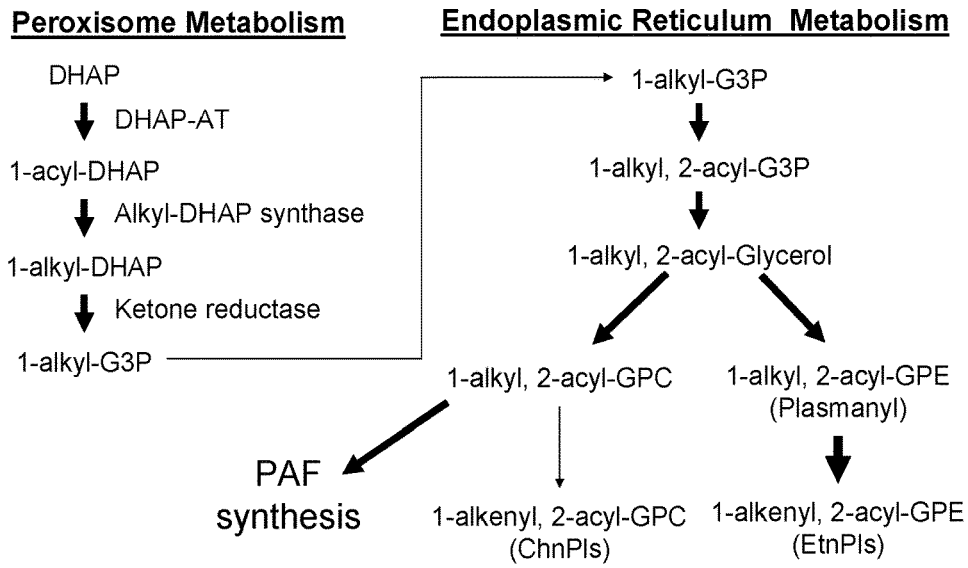
FIG. 22 shows the biosynthetic pathway of plasmalogens in mammals.

Determination of Whether Decreased Levels are Due to Increased Oxidative Degradation of Plasmalogens As is shown in FIGS. 1 and 22, the final step in plasmalogen synthesis occurs in the ER and involves the desaturation of the 1-O-ether to the 1-O-vinyl ether. This 1-O-vinyl ether is critical to many of the properties of plasmalogens, especially their anti-oxidant capacity. Any situation that results in an increase in oxidative stress remote from the synthesis would preferentially deplete the plasmenyl species. To investigate this, the plasmanyl/plasmenyl pairs for 16:0/18:2 and 16:0/22:6 were measured (FIG. 4). What we observed was that in the diseases that showed a decrease in serum plasmalogen levels, both the plasmanyl and plasmenyl species decreased together. This indicates that the decreased levels of plasmalogens in cancer and dementia are not due to increased oxidative stress in these diseases.

Determination of Prevalence of AO-PBD in Different Age Groups and Diseases

Figure 14:
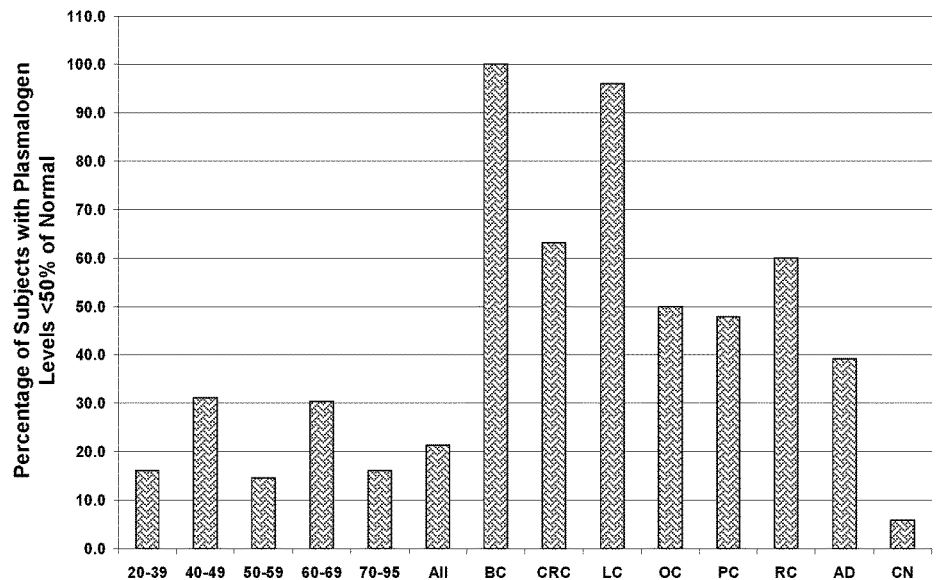
FIG. 14 shows the percentage of subjects with serum plasmalogen levels less than 50% of normal levels.

To determine the prevalence of AO-PBD we first calculated the plasmenyl 16:0/18:2 and plasmenyl 16:0/22:6 ratio to diacyl 16:0/18:0 for all of the subjects, then we divided each subject by the normal population mean and then log 2 normalized each value. The lowest of the two log 2 values for each subject was then used to create the population histograms shown in FIGS. 5 to 13. A cut-off value of −1 was used, however any cut-value that yields the desired sensitivity and specificity could be used. Subjects with log 2 values less than −1 have serum plasmalogen levels less than 50% of the population average. To put this in perspective, the RDCP cell lines used by Perichon[11] had plasmalogen levels of approximately 30% of controls. Using this cut-off it was observed that the prevalence in cancer ranged from just under 50% in prostate cancer to 100% in breast cancer (FIG. 14). The difference between dementia subjects and cognitively confirmed normals was 39% vs 6%, respectively.

Since a comorbidity between cancer and dementia is not obvious[12], and a common underlying biochemical abnormality between cancer and dementia has never before been established. These data strongly indicate that AO-PBD is not a symptom of cancer or dementia and must therefore have an etiology of its own.

Investigations into the Etiology of AO-PBD

Figure 15:
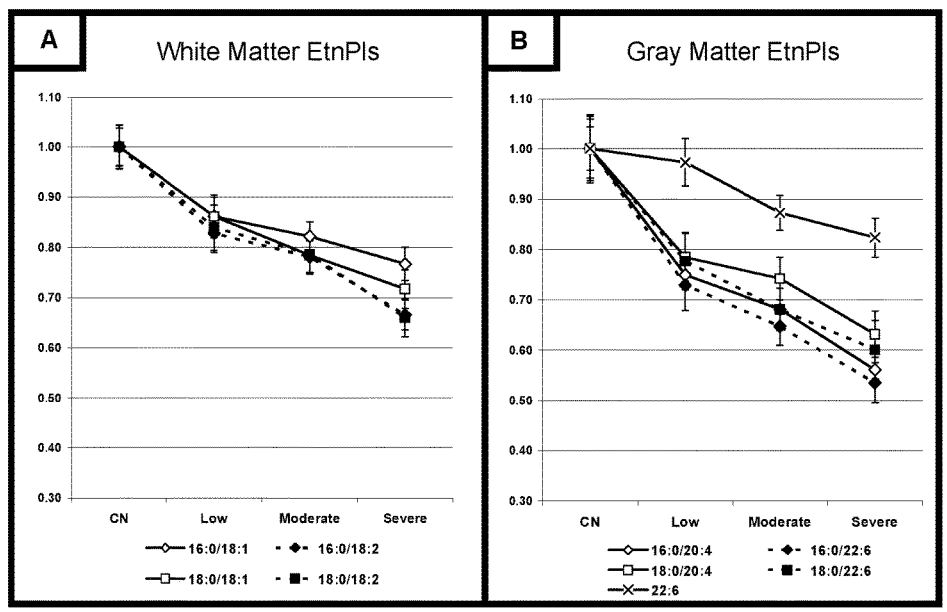
FIG. 15 shows the effect of dementia severity and SDAT pathology on serum PlsEtn levels (SDAT: Senile Dementia of the Alzheimer's Type).

Since the etiology of dementia has been extensively studied, we determined the effect of dementia severity using 324 subjects (176 female, 148 male) aged 56 to 95, comprised of 68 cognitively confirmed non-demented subjects (Mini Mental State Examination (MMSE≥28)) and 256 subjects currently diagnosed as having dementia (Alzheimer's Diseases Assessment Score, cognitive sub-set (ADAS-cog) 6-70, MMSE 0-26)). Subjects were grouped into one of four dementia severity cohorts based upon either their MMSE score [≥28=Cognitively Normal] or their ADAS-cog score [5-19=low cognitive impairment; 20-39=moderate; 40-70=severe]. Mean serum levels of eight PlsEtn and free docosahexaenoic acid (DHA, 22:6) were determined for each group (FIG. 15). All eight PlsEtn in all dementia subgroups were observed to be significantly reduced relative to cognitive controls (24 pair-wise comparisons, t-test p-values 2.6e-2 to 2.0e-10, median=3.9e-5). Free DHA was significantly decreased only in moderately and severely demented subjects ($p<0.05$).

Figure 16:
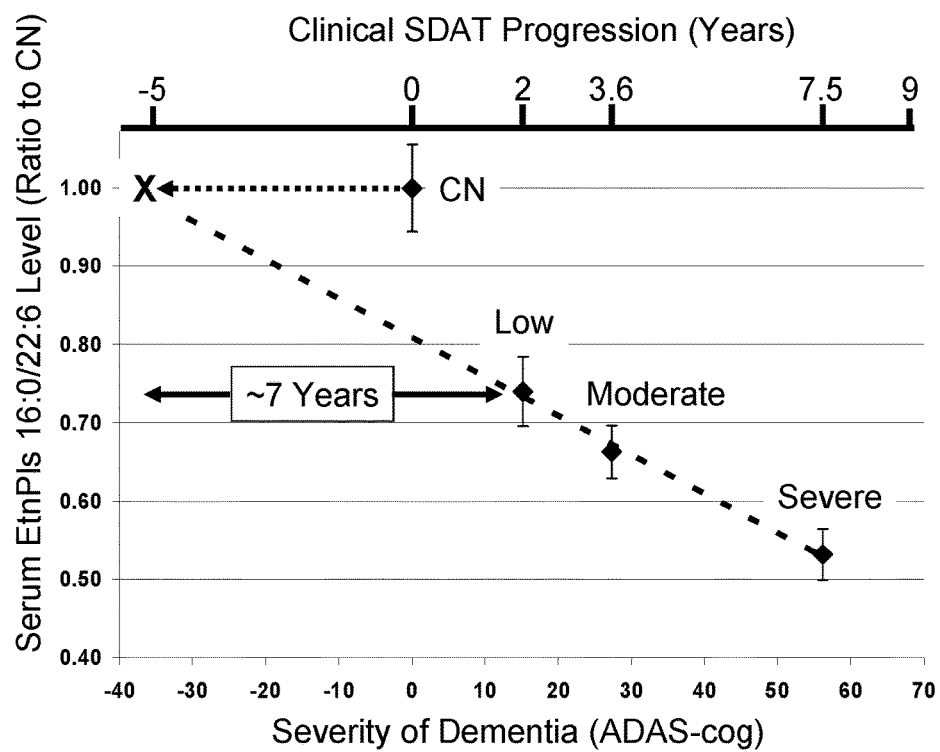
FIG. 16 shows the linear regression analysis of disease severity and serum PlsEtn 16:0/22:6 levels in 256 SDAT subjects. X=predicted time of AO-PBD occurrence. Values are expressed as mean±SEM (n=66-112). Clinical progression assumes 7.5 ADAS-cog points/year.
Figure 17:
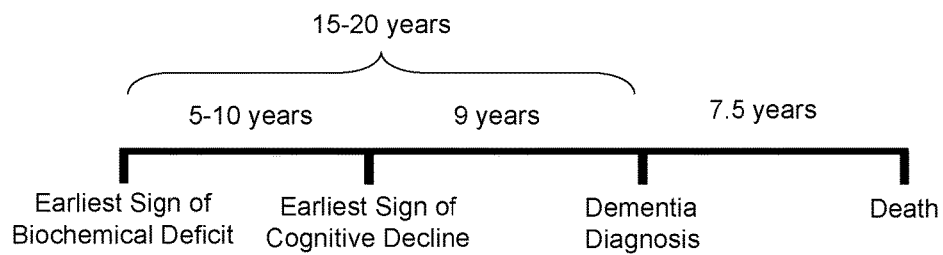
FIG. 17 shows the etiology of dementia.

The data in FIG. 15 indicate that decreased serum PlsEtn correlate with increasing dementia. To investigate this concept in detail, we performed a linear regression analysis using the mean serum PlsEtn 16:0/22:6 level (normalized to CN) of each of the dementia cohorts and the average ADAS-cog score for each of these three cohorts (FIG. 16). A very high correlation was observed between the mean serum PlsEtn 16:0/22:6 level and the mean ADAS-cog scores of the three dementia cohorts ($r^2=0.99$). However, this linear decrease did not extrapolate back to the CN group (X vs. CN). Assuming a clinical dementia progression of 7.5 ADAS-cog units per year this extrapolation predicts that that PlsEtn 16:0/22:6 levels begin to decline at least seven years before clinical cognitive impairment (ADAS-cog=15) is evident. These data are consistent with the recent findings of Amieva et al[13] in which a nine year prodromal phase of dementia of the Alzheimer's type was observed. Considering that the effects of biochemical changes are rarely linear, but more commonly reflect an exponential effect, the prodromal biochemical phase would be expected to be longer than the prodromal clinical phase. This is supported by the fact that amyloid plaques begin to accumulate in 40-49 year olds[14] but Alzheimer's does not begin to clinically manifest until late 60's early 70's. Based upon these two studies and our own evidence that serum plasmalogens decrease before clinical symptoms occur, the etiology of dementia can be expressed according to FIG. 17.

Figure 18:
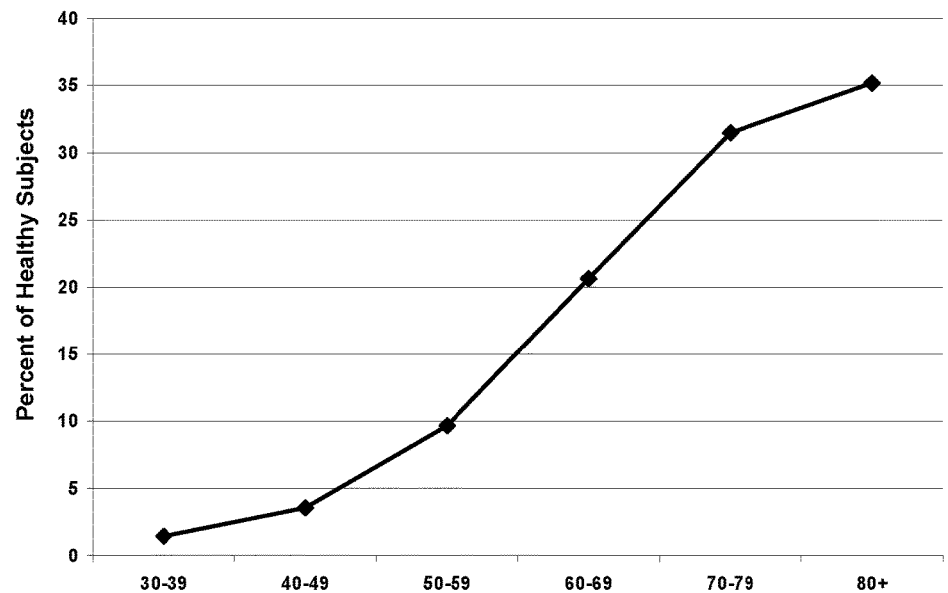
FIG. 18 shows the percentage of healthy subjects predicted to get cancer in the next 15 years.
Figure 19:
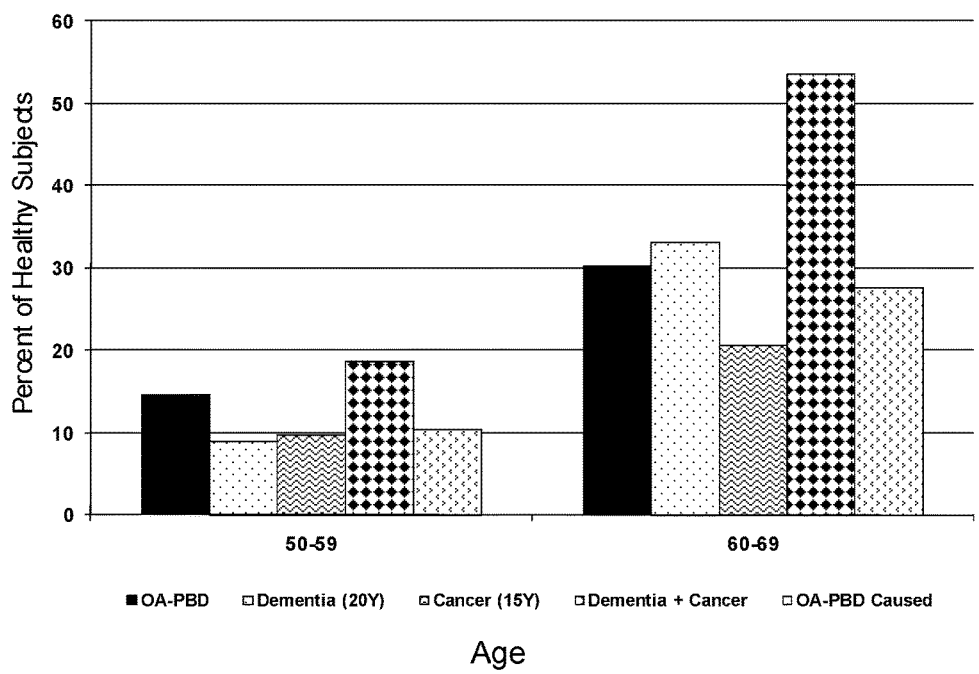
FIG. 19 shows the percentage of healthy 50-59 and 60-69 year-olds with age-related plasmalogen deficiency, predicted to get dementia within 20 years or cancer within 15 years, and the percentage of those cases predicted to be attributed to age-related plasmalogen deficiency.

Furthermore, most cancers are predicted to have a 10-15 year prodromal period. Assuming a 15 year prodromal period for cancer, the percentage of asymptomatic subjects that will get cancer in the next 15 years can be calculated (FIG. 18). Similar calculations can be made for dementia. All values were calculated based upon Canadian cancer and dementia statistics. FIG. 19 displays the actual prevalence of AO-PBD in asymptomatic population controls aged 50-59 and 60-69. These values are compared to the percentage of asymptomatic subjects that will get either cancer in 15 years or dementia in 20 years followed by the sum of these two populations. The last column shows, based upon the prevalence of AO-PBD in these diseases (40% for dementia and 70% for cancer), what percentage of these subjects would be expected to have contracted cancer or dementia as a result of having a pre-existing disease of AO-PBD. What this analysis revealed is that of 50-59 year-olds 20% would be expected to get either cancer or dementia in the next 15-20 years and 40% of 60-69 year-olds will get either cancer or dementia. These data are remarkably close to the observed prevalence of AO-PBD in 50-59 (15%) and 60-69 year-olds (30%).

Figure 20:
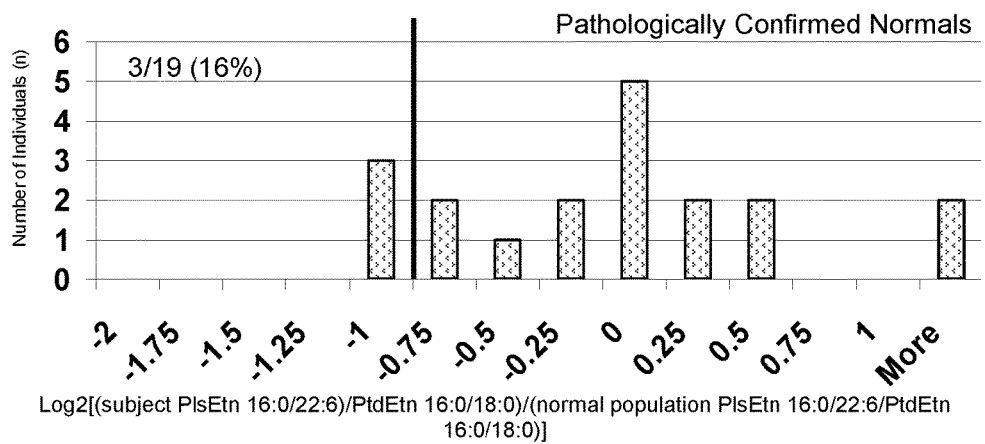
FIG. 20 shows the distribution of plasmenyl 16:0/22:6 in autopsy-confirmed non-Alzheimer's subjects.
Figure 21:
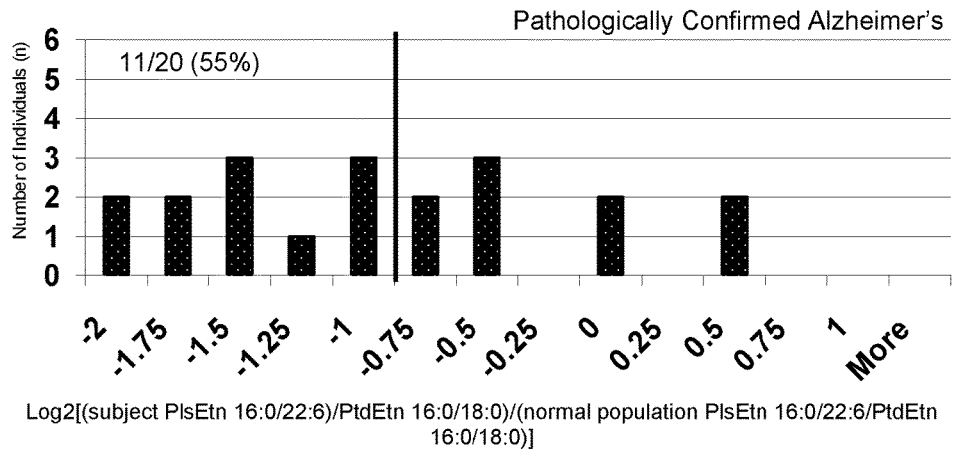
FIG. 21 shows the distribution of plasmenyl 16:0/22:6 in autopsy-confirmed Alzheimer's subjects.

To be confident that, in dementia, that AO-PBD was not simply a result of Alzheimer's Disease (AD) pathology, we investigated serum samples collected from 20 subjects (10 male and 10 female), pathologically confirmed to have AD and 19 subjects pathologically confirmed not to have AD. As can be seen by FIGS. 20 and 21, AO-PBD is present in only 55% of the AD cases and in 16% of the controls. This means that in 45% of AD subjects, the underlying cause is something other than AO-PBD. Clearly AO-PBD and AD are not the same disease.

What the above studies show is that AO-PBD shows a separate and distinct etiology from both cancer and dementia. Whereas the prevalence of cancer and dementia continue to increase with increasing age to at least age 90, the prevalence of AO-PBD peaks at age 60-69 and then decreases from age 70 onward. Furthermore although AO-PBD exhibits a similar biochemical profile to RCDP, it should not be confused with RCDP. The three forms of RDCP are all genetic disorders that affect children. Although, the underlying cause of AO-PBD is at this time unknown, it is certainly not an inborn error of metabolism. The relationship between RCDP and AO-PBD is similar to the relationship between Down's syndrome (a genetically determined disease) and Alzheimer's Disease (an adult onset disease of unknown cause). Both Down's syndrome and Alzheimer's Disease exhibit similar biochemical features (i.e. accumulation of amyloid plaques in the brain), but the clinical manifestations are dramatically different.

Example 2

Identification of Subjects that have AO-PBD Using Serum Levels of Metabolites Using a validated analytical method such as that described above in Example 1, the mean±SEM serum levels for all or a subset of all of the metabolites listed in Table 5 were measured for a plurality of cognitively normal, cancer-free subjects. This can be done for males and females separately or combined. The mean value for each metabolite so measured becomes the normal reference value.

Using a validated analytical method such as that described above, the serum level of each or a subset of all of the metabolites listed in Table 5 for test subject were calculated.

The ratio of the serum level of the test subject to average serum level of the normal population was then determined and this ratio was compared to a cut-off value (for example, but not meant to be limiting, a value of 0.5 was used throughout this application). Subjects with a ratio of less than 0.5 are deemed to have AO-PBD.

Example 3

Identification of Subjects that have AO-PBD Using a Mathematically Determined Plasmalogen Score of the Ratio of Serum Levels of Metabolites Listed in Table 5 to an Endogenous Reference Metabolite Using a validated analytical method such as that described above in Example 1, the mean±SEM serum levels for all or a subset of all of the metabolites listed in Table 5 for a plurality of cognitively normal, cancer-free subjects was determined. This can be done for males and females separately or combined.

The ratio of these metabolites to the corresponding average from the cognitively normal or known dementia cohort was determined. The data was transformed to log 2, as described in Example 1. The lowest log 2 score of M16 and M19 was selected. The log 2 score was then compared to a cut-off value (−1.0 is used in this application) to determine if a subject has AO-PBD.

Example 4

Identification of AO-PBD Subjects by Comparing the Ratio of One or More than One Metabolite to an Endogenous Reference Metabolite from a Test Subject to the Average Such Ratio from a Normal Reference Population In order to decrease patient to patient variability, an endogenous metabolite that does not change significantly between the variables being tested can be used. For example, M01 could be used as it does not change significantly in AO-PBD. Using a validated analytical method such as that described above, the ratio of all or a subset of all of the metabolites listed in Table 5 was calculated. The mean±SEM serum ratio levels for each of these metabolites for a plurality of normal subjects was also calculated. This can be done for males and females separately or combined.

The serum ratio levels of one or more than one of the metabolites listed in Table 5 for a subject of unknown AO-PBD status was also determined. The ratio of one or more than one these metabolites to the corresponding average normal concentration was calculated and compared to a cut-off value. This comparison was used to determine if said subject has AO-PBD.

All citations are hereby incorporated by reference.

The present invention has been described with regard to one or more embodiments. However, it will be apparent to persons skilled in the art that a number of variations and modifications can be made without departing from the scope of the invention as defined in the claims.

TABLE 1

Biochemical functions performed by peroxisomes

| | |
|---|---|
| 1. | Etherphospholipid biosynthesis |
| 2. | Fatty acid β-oxidation |
| 3. | Fatty acid α-oxidation |
| 4. | Glyoxylate detoxification |
| 5. | Biosynthesis of cholesterol and dolichol |
| 6. | Pipecolic acid degradation |
| 7. | Biosynthesis of docosahexaenoic acid |
| 8. | Hydrogen peroxide metabolism |
| 9. | Aminoacid metabolism |

TABLE 2

Peroxisomal disorders and their enzymatic basis

| | | |
|---|---|---|
| 1. | Cerebro-hepato-renal syndrome of Zellweger (ZS) | Generalized |
| 2. | Neonatal adrenoleukodystrophy (NALD) | Generalized |
| 3. | Infantile Refsum disease (IRD) | Generalized |
| 4. | Hyperpipecolic acidaemia (HPA) | Generalized |
| 5. | RCDP Type 1 (PTS2-receptor defect) | Multiple |
| 6. | RCDP Type 2 (DHAPAT-deficiency) | DHAPAT |
| 7. | RCDP Type 3 (AlkylDHAP-synthase deficiency) | AlkylDHAP-synthase |
| 8. | Zellweger-like syndrome | Multiple |
| 9. | X-linked adrenoleukodystrophy (XALD) | ALDp |
| 10. | Acyl-CoA oxidase deficiency (pseudo-NALD) | Acyl-CoA oxidase |
| 11. | Bifunctional protein deficiency | D-Bifunctional protein |
| 12. | Perioxisomal thiolase (I) deficiency | Thiolase (peroxisomal) |
| 13. | Hyperoxaluria Type 1 (alanine glyoxylate aminotransferase deficiency | AGT |
| 14. | Refsum disease (classic form) (phytanoyl-CoA hydroxylase deficiency) | Phytanoyl-CoA hydroxylase |
| 15. | Glutaric aciduria Type 3 | Glutaryl-CoA oxidase |
| 16. | Mevalonate kinase deficiency | Melalonate kinase |
| 17. | Acatalasaemia | Catalase |

Abbreviations used:
DHAPAT = DiHydroxyAcetonePhosphate AcylTransferase;
AGT = Alanine Glyoxylate aminoTransferase;
PhyH = Phytanoyl-CoA Hydroxylase;
ALDp = AdrenoLeukoDystrophy protein;
RCDP = Rhizomelic ChondroDysplasia Punctata.

TABLE 3

Differentiation of peroxisomal disorders:
Biogenesis vs. single enzyme deficiencies.

Group 1 (Biogenesis defects)

Zellweger syndrome
Neonatal adrenoleukodystrophy
Infantile Refsum disease
Hyperpipecolic acidemia
Rhizomelic chondrodysplasia punctata (RCDP) Type 1
Zellweger-like syndrome*
Group 2 (Single Enzyme (Protein) deficiencies):

X-linked adrenoleukodystrophy
Acyl-CoA oxidase deficiency
Bifunctional protein deficiency

TABLE 3-continued

Differentiation of peroxisomal disorders:
Biogenesis vs. single enzyme deficiencies.

Peroxisomal thiolase deficiency
Rhizomelic chondrodysplasia punctata Type 2 (DHAPAT-deficiency)
Rhizomelic chondrodysplasia punctata Type 3 (alkylDHAP synthase deficiency)
Refsum disease (Classic type) (phytanoyl-CoA hydroxylase deficiency)
Glutaric aciduria Type 3 (glutaryl-CoA oxidase deficiency)
Mevalonate kinase deficiency
Hyperoxaluria Type 1 (alanine glyoxylate aminotransferase deficiency)
Acatalasaemia

*Not established definitively

TABLE 4

Clinical Data Summary

| Disease | Age (Mean) | Age (SEM) | Male | Female | n |
|---|---|---|---|---|---|
| Control, All | 56.6 | 0.6 | 184 | 253 | 437 |
| Control, 20-39 | 33.9 | 0.9 | 12 | 19 | 31 |
| Control, 40-49 | 44.8 | 0.4 | 29 | 45 | 74 |
| Control, 50-59 | 54.1 | 0.2 | 64 | 107 | 171 |
| Control, 60-69 | 64.0 | 0.3 | 44 | 55 | 99 |
| Control, 70-95 | 77.3 | 0.7 | 35 | 27 | 62 |
| Cognitive Normal | 77.2 | 0.8 | 32 | 36 | 68 |
| Alzheimer's Disease | 80.3 | 0.5 | 79 | 114 | 194 |
| Relapsing/Remitting | 47.6 | 0.6 | 54 | 231 | 285 |
| Secondary Progressive | 51.3 | 2.0 | 8 | 16 | 24 |
| Primary Progressive | 54.5 | 1.8 | 5 | 11 | 16 |
| Colon Cancer | 60.3 | 1.0 | 131 | 89 | 220 |
| Ovarian Cancer | 60.7 | 2.9 | 0 | 20 | 20 |
| Prostate Cancer | 63.1 | 1.9 | 25 | 0 | 25 |
| Lung Cancer | 61.2 | 2.6 | 11 | 14 | 25 |
| Renal Cancer | 67.6 | 2.2 | 17 | 13 | 30 |
| Breast Cancer | 57.5 | 2.6 | 0 | 25 | 25 |

TABLE 6

Table of serum changes (relative to controls) for diacyl GPEs.

| | Diacyl GPEs | | | |
|---|---|---|---|---|
| Raw IS Ratio Data | 16:0/18:0 718.0/255.0 | 16:0/18:1 716.0/255.0 | 18:0/18:0 746.0/283.0 | 18:0/18:1 744.0/283.0 |
| AD, All | 1.01 | 0.97 | 0.80 | 1.02 |
| | 7.1E−01 | 6.2E−01 | 2.9E−06 | 7.7E−01 |
| RR, All | 0.74 | 0.91 | 0.82 | 0.93 |
| | 3.2E−18 | 5.4E−02 | 3.3E−07 | 1.5E−01 |
| RR, 20-29 | 0.86 | 1.17 | 0.82 | 1.08 |
| | 6.8E−01 | 8.6E−02 | 3.0E−01 | 3.5E−01 |
| RR, 30-39 | 0.81 | 1.13 | 0.84 | 0.91 |
| | 4.8E−02 | 4.7E−01 | 1.5E−01 | 6.2E−01 |
| RR, 40-49 | 0.66 | 0.68 | 0.76 | 0.73 |
| | 2.0E−09 | 9.3E−05 | 5.0E−04 | 2.7E−03 |
| RR, 50-59 | 0.82 | 0.99 | 0.86 | 1.01 |
| | 1.4E−03 | 9.2E−01 | 1.8E−02 | 9.1E−01 |
| RR, 60-69 | 0.70 | 0.87 | 0.87 | 0.92 |
| | 3.4E−04 | 3.2E−01 | 2.0E−01 | 5.8E−01 |
| Secondary Progressive | 1.01 | 1.33 | 1.37 | 1.52 |
| | 8.9E−01 | 1.2E−02 | 7.3E−04 | 3.6E−04 |
| Primary Progressive | 0.88 | 0.97 | 1.08 | 1.00 |
| | 2.9E−01 | 8.4E−01 | 5.3E−01 | 9.9E−01 |
| Colon Cancer, All | 1.13 | 0.99 | 0.92 | 0.69 |
| | 2.7E−03 | 7.9E−01 | 5.5E−02 | 2.1E−09 |
| Ovarian Cancer | 1.09 | 0.87 | 0.89 | 0.73 |
| | 3.7E−01 | 3.6E−01 | 3.3E−01 | 7.3E−02 |
| Prostate Cancer | 0.93 | 0.73 | 0.73 | 0.59 |
| | 4.2E−01 | 3.1E−02 | 8.9E−03 | 2.8E−03 |
| Lung Cancer | 1.33 | 1.03 | 0.76 | 0.79 |
| | 9.2E−04 | 8.1E−01 | 2.7E−02 | 1.6E−01 |
| Renal Cancer | 1.62 | 1.43 | 1.12 | 1.36 |
| | 7.1E−13 | 2.8E−01 | 2.1E−01 | 6.0E−03 |
| Breast Cancer | 1.17 | 0.90 | 0.71 | 0.60 |
| | 6.1E−02 | 4.2E−01 | 6.1E−03 | 3.3E−03 |

Note:
IS stands for Internal Standard (PtdEtn 16:0/18:0); AD stands for Alzheimer's Disease; and RR stands for Relapsing/Remitting Multiple Sclerosis.

TABLE 5

Table of Diacyl, Plasmanyl, and Plasmenyl GPEs and Free Fatty Acids Measured in Serum.

| Metabolite Code | Metabolite Name | Molecular Formula | Parent Mass | M-H Mass | Diagnostic Fragment Mass | MS/MS Transition |
|---|---|---|---|---|---|---|
| M01 | PtdEt 16:0/18:0 | C39H78N1O8P1 | 719.54648 | 718.5 | R1 (C16H31O2) − 255 | 718.0/255.0 |
| M02 | PtdEt 16:0/18:1 | C39H76N1O8P1 | 717.53083 | 716.5 | R1 (C16H31O2) − 255 | 716.0/255.0 |
| M03 | PtdEt 18:0/18:0 | C41H82N1O8P1 | 747.57777 | 746.5 | R1 (C18H35O2) − 283 | 746.0/283.0 |
| M04 | PtdEt 18:0/18:1 | C41H80N1O8P1 | 745.56213 | 744.5 | R1 (C18H35O2) − 283 | 744.0/283.0 |
| M05 | Plasmanyl 16:0/18:1 | C39H78N1O7P1 | 703.55156 | 702.5 | R2 (C18H33O2) − 281 | 702.0/281.0 |
| M06 | Plasmanyl 16:0/18:2 | C39H76N1O7P1 | 701.53591 | 700.5 | R2 (C18H31O2) − 279 | 700.0/279.0 |
| M07 | Plasmanyl 16:0/20:4 | C41H76N1O7P1 | 725.53591 | 724.5 | R2 (C20H31O2) − 303 | 724.0/303.0 |
| M08 | Plasmanyl 16:0/22:4 | C43H80N1O7P1 | 753.56721 | 752.5 | R2 (C22H35O2) − 331 | 752.0/331.0 |
| M09 | Plasmanyl 16:0/22:6 | C43H76N1O7P1 | 749.53591 | 748.5 | R2 (C22H31O2) − 327 | 748.0/327.0 |
| M10 | Plasmanyl 18:0/18:1 | C41H82N1O7P1 | 731.58286 | 730.5 | R2 (C18H33O2) − 281 | 730.0/281.0 |
| M11 | Plasmanyl 18:0/18:2 | C41H80N1O7P1 | 729.56721 | 728.5 | R2 (C18H31O2) − 279 | 728.0/279.0 |
| M12 | Plasmanyl 18:0/20:4 | C43H80N1O7P1 | 753.56721 | 752.5 | R2 (C20H31O2) − 303 | 752.0/303.0 |
| M13 | Plasmanyl 18:0/22:4 | C45H84N1O7P1 | 781.59851 | 780.5 | R2 (C22H35O2) − 331 | 780.0/331.0 |
| M14 | Plasmanyl 18:0/22:6 | C45H80N1O7P1 | 777.56721 | 776.5 | R2 (C22H31O2) − 327 | 776.0/327.0 |
| M15 | Plasmenyl 16:0/18:1 | C39H76N1O7P1 | 701.53591 | 700.5 | R2 (C18H33O2) − 281 | 700.0/281.0 |
| M16 | Plasmenyl 16:0/18:2 | C39H74N1O7P1 | 699.52026 | 698.5 | R2 (C18H31O2) − 279 | 698.0/279.0 |
| M17 | Plasmenyl 16:0/20:4 | C41H74N1O7P1 | 723.52026 | 722.5 | R2 (C20H31O2) − 303 | 722.0/303.0 |
| M18 | Plasmenyl 16:0/22:4 | C43H78N1O7P1 | 751.55156 | 750.5 | R2 (C22H35O2) − 331 | 750.0/331.0 |
| M19 | Plasmenyl 16:0/22:6 | C43H74N1O7P1 | 747.52026 | 746.5 | R2 (C22H31O2) − 327 | 746.0/327.0 |
| M20 | Plasmenyl 18:0/18:1 | C41H80N1O7P1 | 729.56721 | 728.5 | R2 (C18H33O2) − 281 | 728.0/281.0 |
| M21 | Plasmenyl 18:0/18:2 | C41H78N1O7P1 | 727.55156 | 726.5 | R2 (C18H31O2) − 279 | 726.0/279.0 |
| M22 | Plasmenyl 18:0/20:4 | C43H78N1O7P1 | 751.55156 | 750.5 | R2 (C20H31O2) − 303 | 750.6/303.2 |
| M23 | Plasmenyl 18:0/22:4 | C45H82N1O7P1 | 779.58286 | 778.5 | R2 (C22H35O2) − 331 | 778.0/331.0 |
| M24 | Plasmenyl 18:0/22:6 | C45H78N1O7P1 | 775.55156 | 774.5 | R2 (C22H31O2) − 327 | 774.0/327.0 |
| M25 | Free 22:6 | C22H32O2 | 328.24022 | 327.2 | (C21H31) − 283 | 327.2/283.0 |
| M26 | Free 20:4 | C20H32O2 | 304.24022 | 303.2 | (C19H31) − 259 | 303.2/259.5 |

TABLE 7

Table of serum changes (relative to controls) for plasmanyl GPEs.

| | Plasmanyl GPEs | | | | | | | | | |
|---|---|---|---|---|---|---|---|---|---|---|
| Raw IS Ratio Data | 16:0/18:1 702.0/ 281.0 | 16:0/18:2 700.0/ 279.0 | 16:0/20:4 724.0/ 303.0 | 16:0/22:4 752.0/ 331.0 | 16:0/22:6 748.0/ 327.0 | 18:0/18:1 730.0/ 281.0 | 18:0/18:2 728.0/ 279.0 | 18:0/20:4 752.0/ 303.0 | 18:0/22:4 780.0/ 331.0 | 18:0/22:6 776.0/ 327.0 |
| AD, All | 0.86 | 0.85 | 0.66 | 0.70 | 0.68 | 0.94 | 0.85 | 0.75 | 0.82 | 0.86 |
| | 7.1E−04 | 3.0E−04 | 4.2E−09 | 4.5E−07 | 1.5E−06 | 1.1E−01 | 6.7E−05 | 2.3E−09 | 7.2E−06 | 2.0E−02 |
| RR, All | 0.81 | 0.88 | 0.79 | 0.84 | 0.81 | 0.90 | 0.94 | 0.87 | 0.89 | 0.91 |
| | 2.8E−08 | 2.9E−04 | 3.1E−05 | 1.3E−03 | 2.7E−04 | 1.8E−03 | 7.4E−02 | 1.7E−04 | 1.3E−03 | 5.8E−02 |
| RR, 20-29 | 0.71 | 0.80 | 0.68 | 0.63 | 0.79 | 0.90 | 1.07 | 0.83 | 0.77 | 1.15 |
| | 2.7E−01 | 5.8E−01 | 9.0E−02 | 3.9E−01 | 3.1E−01 | 4.5E−01 | 5.8E−02 | 5.0E−01 | 8.9E−01 | 2.6E−01 |
| RR, 30-39 | 0.73 | 0.71 | 0.67 | 0.71 | 0.83 | 0.91 | 0.77 | 0.80 | 0.86 | 1.00 |
| | 9.1E−03 | 6.2E−03 | 8.0E−03 | 1.6E−02 | 2.6E−01 | 4.3E−01 | 3.3E−02 | 5.4E−02 | 1.6E−01 | 1.0E+00 |
| RR, 40-49 | 0.72 | 0.78 | 0.74 | 0.70 | 0.74 | 0.77 | 0.83 | 0.80 | 0.77 | 0.85 |
| | 1.7E−05 | 8.2E−04 | 1.6E−02 | 1.6E−03 | 2.9E−02 | 1.3E−04 | 6.8E−03 | 3.5E−03 | 1.1E−04 | 1.3E−01 |
| RR, 50-59 | 0.85 | 0.89 | 0.76 | 0.83 | 0.79 | 0.96 | 0.99 | 0.87 | 0.91 | 0.94 |
| | 6.7E−03 | 5.2E−02 | 1.2E−03 | 2.1E−02 | 8.8E−03 | 4.8E−01 | 8.0E−01 | 2.5E−02 | 9.7E−02 | 3.9E−01 |
| RR, 60-69 | 0.77 | 0.93 | 0.84 | 0.85 | 0.94 | 0.85 | 0.92 | 0.91 | 0.94 | 1.10 |
| | 3.1E−02 | 4.7E−01 | 3.0E−01 | 3.4E−01 | 7.2E−01 | 1.0E−01 | 3.5E−01 | 4.0E−01 | 6.0E−01 | 4.9E−01 |
| Secondary Progressive | 1.27 | 1.36 | 1.49 | 1.35 | 1.77 | 1.31 | 1.35 | 1.36 | 1.36 | 1.76 |
| | 1.1E−02 | 6.7E−04 | 1.6E−03 | 2.2E−02 | 1.9E−05 | 1.1E−03 | 1.7E−04 | 5.7E−04 | 3.1E−04 | 8.0E−08 |
| Primary Progressive | 0.94 | 1.09 | 1.09 | 1.00 | 1.24 | 1.01 | 1.05 | 1.10 | 1.10 | 1.29 |
| | 6.1E−01 | 5.0E−01 | 6.2E−01 | 9.9E−01 | 2.3E−01 | 9.2E−01 | 6.4E−01 | 4.1E−01 | 4.2E−01 | 7.9E−02 |
| Colon Cancer, All | 0.80 | 0.61 | 0.67 | 0.62 | 0.69 | 0.89 | 0.63 | 0.78 | 0.84 | 0.99 |
| | 7.7E−06 | 1.5E−20 | 2.2E−08 | 2.2E−12 | 1.5E−07 | 4.8E−03 | 2.6E−24 | 1.5E−08 | 2.5E−05 | 8.1E−01 |
| Ovarian Cancer | 0.82 | 0.70 | 0.63 | 0.59 | 0.70 | 0.94 | 0.74 | 0.76 | 0.78 | 1.13 |
| | 1.1E−01 | 9.3E−03 | 2.2E−02 | 1.1E−02 | 9.0E−02 | 5.6E−01 | 8.2E−03 | 3.2E−02 | 4.5E−02 | 3.8E−01 |
| Prostate Cancer | 0.68 | 0.63 | 0.49 | 0.63 | 0.55 | 0.79 | 0.70 | 0.67 | 0.82 | 0.72 |
| | 1.8E−03 | 3.4E−04 | 3.6E−04 | 1.1E−02 | 5.1E−03 | 1.9E−02 | 6.9E−04 | 7.4E−04 | 6.1E−02 | 3.4E−02 |
| Lung Cancer | 0.66 | 0.55 | 0.35 | 0.36 | 0.29 | 0.89 | 0.69 | 0.62 | 0.73 | 0.55 |
| | 1.4E−03 | 1.2E−05 | 6.5E−06 | 1.6E−05 | 8.5E−06 | 2.6E−01 | 8.6E−04 | 1.8E−04 | 6.4E−03 | 7.8E−04 |
| Renal Cancer | 1.15 | 0.97 | 0.72 | 0.91 | 0.85 | 1.29 | 1.05 | 0.91 | 1.08 | 1.24 |
| | 1.2E−01 | 7.1E−01 | 3.5E−02 | 5.1E−01 | 3.0E−01 | 9.9E−04 | 5.5E−01 | 3.4E−01 | 3.9E−01 | 4.8E−02 |
| Breast Cancer | 0.67 | 0.55 | 0.39 | 0.45 | 0.36 | 0.87 | 0.64 | 0.63 | 0.79 | 0.51 |
| | 1.3E−03 | 8.8E−06 | 2.6E−05 | 1.6E−04 | 6.8E−05 | 1.7E−01 | 4.8E−05 | 2.2E−04 | 3.2E−02 | 1.9E−04 |

Note:
IS stands for Internal Standard (PtdEtn 16:0/18:0); AD stands for Alzheimer's Disease; and RR stands for Relapsing/Remitting Multiple Sclerosis.

TABLE 8

Table of serum changes (relative to controls) for plasmenyl GPEs.

| | Plasmenyl Pes | | | | | | | | | |
|---|---|---|---|---|---|---|---|---|---|---|
| Raw IS Ratio Data | 16:0/18:1 700.0/ 281.0 | 16:0/18:2 698.0/ 279.0 | 16:0/20:4 722.0/ 303.0 | 16:0/22:4 750.0/ 331.0 | 16:0/22:6 746.0/ 327.0 | 18:0/18:1 728.0/ 281.0 | 18:0/18:2 726.0/ 279.0 | 18:0/20:4 750.6/ 303.2 | 18:0/22:4 778.0/ 331.0 | 18:0/22:6 774.0/ 327.0 |
| AD, All | 0.82 | 0.78 | 0.66 | 0.70 | 0.72 | 0.85 | 0.80 | 0.76 | 0.74 | 0.80 |
| | 7.5E−07 | 4.7E−08 | 4.0E−09 | 2.6E−08 | 7.6E−06 | 3.3E−04 | 7.0E−06 | 1.7E−05 | 6.5E−08 | 1.5E−03 |
| RR, All | 0.84 | 0.88 | 0.80 | 0.85 | 0.82 | 0.84 | 0.90 | 0.81 | 0.83 | 0.85 |
| | 1.0E−07 | 4.4E−04 | 1.3E−04 | 1.1E−03 | 6.5E−04 | 6.1E−06 | 6.5E−03 | 1.6E−04 | 4.2E−05 | 4.4E−03 |
| RR, 20-29 | 0.77 | 0.81 | 0.60 | 0.62 | 0.78 | 0.69 | 0.82 | 0.62 | 0.67 | 0.71 |
| | 3.8E−01 | 5.1E−01 | 7.2E−02 | 3.5E−01 | 2.9E−01 | 1.5E−01 | 4.5E−01 | 4.8E−02 | 2.5E−01 | 1.1E−01 |
| RR, 30-39 | 0.76 | 0.71 | 0.70 | 0.73 | 0.85 | 0.70 | 0.70 | 0.70 | 0.72 | 0.86 |
| | 1.2E−02 | 4.4E−03 | 3.8E−02 | 3.4E−02 | 3.7E−01 | 9.1E−03 | 1.2E−02 | 4.0E−02 | 1.5E−02 | 4.2E−01 |
| RR, 40-49 | 0.73 | 0.82 | 0.77 | 0.72 | 0.81 | 0.75 | 0.80 | 0.78 | 0.74 | 0.81 |
| | 4.3E−06 | 4.5E−03 | 3.2E−02 | 9.6E−04 | 8.7E−02 | 1.7E−04 | 5.4E−03 | 2.1E−02 | 2.0E−04 | 8.4E−02 |
| RR, 50-59 | 0.90 | 0.91 | 0.79 | 0.84 | 0.82 | 0.90 | 0.93 | 0.80 | 0.83 | 0.86 |
| | 5.2E−02 | 1.3E−01 | 1.2E−02 | 3.0E−02 | 2.8E−02 | 1.0E−01 | 2.8E−01 | 1.5E−02 | 7.5E−03 | 1.2E−02 |
| RR, 60-69 | 0.84 | 0.90 | 0.85 | 0.90 | 0.94 | 0.87 | 0.95 | 0.90 | 0.87 | 1.03 |
| | 7.0E−02 | 3.2E−01 | 3.1E−01 | 5.5E−01 | 7.0E−01 | 2.4E−01 | 6.5E−01 | 4.7E−01 | 4.4E−01 | 8.5E−01 |
| Secondary Progressive | 1.15 | 1.27 | 1.36 | 1.47 | 1.69 | 1.25 | 1.33 | 1.46 | 1.41 | 1.77 |
| | 1.1E−01 | 1.0E−02 | 1.8E−02 | 1.1E−03 | 4.0E−05 | 2.0E−02 | 5.4E−03 | 1.7E−03 | 8.7E−04 | 3.0E−06 |
| Primary Progressive | 0.94 | 1.04 | 1.11 | 1.03 | 1.29 | 1.03 | 1.11 | 1.18 | 1.09 | 1.46 |
| | 6.2E−01 | 7.4E−01 | 5.7E−01 | 8.7E−01 | 1.4E−01 | 8.4E−01 | 4.3E−01 | 3.1E−01 | 5.6E−01 | 1.7E−02 |
| Colon Cancer, All | 0.94 | 0.62 | 0.62 | 0.61 | 0.75 | 0.83 | 0.56 | 0.59 | 0.66 | 0.75 |
| | 1.6E−01 | 1.5E−20 | 6.3E−11 | 1.6E−14 | 3.0E−05 | 1.5E−04 | 1.7E−23 | 1.2E−13 | 2.1E−14 | 1.6E−05 |
| Ovarian Cancer | 0.89 | 0.68 | 0.68 | 0.66 | 0.82 | 0.82 | 0.65 | 0.69 | 0.68 | 0.87 |
| | 2.8E−01 | 4.6E−03 | 5.8E−02 | 2.4E−02 | 3.1E−01 | 1.2E−01 | 5.8E−03 | 4.9E−02 | 1.7E−02 | 4.5E−01 |
| Prostate Cancer | 0.74 | 0.62 | 0.49 | 0.66 | 0.66 | 0.64 | 0.57 | 0.53 | 0.71 | 0.63 |
| | 3.5E−03 | 1.7E−04 | 6.2E−04 | 1.3E−02 | 2.7E−02 | 5.9E−04 | 1.2E−04 | 7.8E−04 | 1.5E−02 | 1.5E−02 |

TABLE 8-continued

Table of serum changes (relative to controls) for plasmenyl GPEs.

|  | Plasmenyl Pes | | | | | | | | | |
|---|---|---|---|---|---|---|---|---|---|---|
| Raw IS Ratio Data | 16:0/18:1 700.0/ 281.0 | 16:0/18:2 698.0/ 279.0 | 16:0/20:4 722.0/ 303.0 | 16:0/22:4 750.0/ 331.0 | 16:0/22:6 746.0/ 327.0 | 18:0/18:1 728.0/ 281.0 | 18:0/18:2 726.0/ 279.0 | 18:0/20:4 750.6/ 303.2 | 18:0/22:4 778.0/ 331.0 | 18:0/22:6 774.0/ 327.0 |
| Lung Cancer | 0.82 | 0.66 | 0.38 | 0.42 | 0.36 | 0.65 | 0.57 | 0.45 | 0.55 | 0.39 |
|  | 5.4E−02 | 8.8E−04 | 3.2E−05 | 2.8E−05 | 4.3E−05 | 1.2E−03 | 1.3E−04 | 8.6E−05 | 1.6E−04 | 7.2E−05 |
| Renal Cancer | 1.08 | 0.88 | 0.75 | 0.90 | 0.94 | 1.03 | 0.81 | 0.80 | 0.92 | 0.96 |
|  | 3.5E−01 | 2.1E−01 | 6.2E−02 | 4.2E−01 | 6.6E−01 | 7.7E−01 | 6.1E−02 | 1.3E−01 | 4.9E−01 | 7.6E−01 |
| Breast Cancer | 0.77 | 0.57 | 0.39 | 0.47 | 0.39 | 0.65 | 0.53 | 0.43 | 0.58 | 0.40 |
|  | 1.1E−02 | 1.8E−05 | 4.4E−05 | 1.0E−04 | 9.1E−05 | 1.0E−03 | 2.5E−05 | 5.3E−05 | 4.1E−04 | 9.7E−05 |

Note:
IS stands for Internal Standard (PtdEtn 16:0/18:0); AD stands for Alzheimer's Disease; and RR stands for Relapsing/Remitting Multiple Sclerosis.

TABLE 9

Table of serum changes (relative to controls) of diacyl GPEs, DHA and AA using diacyl 16:0/18:0 GPE as an internal standard.

|  | Diacyl GPEs | | | | DHA | AA |
|---|---|---|---|---|---|---|
|  | 16:0/18:0 718.0/255.0 | 16:0/18:1 716.0/255.0 | 18:0/18:0 746.0/283.0 | 18:0/18:1 744.0/283.0 | 22:6 327.2/283.0 | 20:4 303.2/259.5 |
| AD, All | 1.00 | 0.89 | 0.76 | 0.93 | 0.70 | 0.71 |
|  | #DIV/0! | 3.3E−04 | 7.4E−19 | 9.0E−02 | 2.1E−10 | 8.0E−12 |
| RR, All | 1.00 | 1.18 | 1.09 | 1.22 | 0.96 | 1.05 |
|  | #DIV/0! | 1.1E−09 | 3.9E−04 | 3.1E−08 | 3.2E−01 | 2.8E−01 |
| RR, 20-29 | 1.00 | 1.19 | 0.94 | 1.14 | 0.75 | 0.83 |
|  | #DIV/0! | 1.1E−02 | 2.3E−01 | 1.3E−01 | 4.2E−02 | 7.5E−02 |
| RR, 30-39 | 1.00 | 1.27 | 1.01 | 1.03 | 1.23 | 0.97 |
|  | #DIV/0! | 1.0E−02 | 8.8E−01 | 8.1E−01 | 1.9E−01 | 8.2E−01 |
| RR, 40-49 | 1.00 | 1.01 | 1.12 | 1.07 | 1.35 | 1.38 |
|  | #DIV/0! | 8.5E−01 | 2.2E−02 | 3.2E−01 | 6.7E−04 | 5.3E−04 |
| RR, 50-59 | 1.00 | 1.18 | 1.03 | 1.23 | 0.80 | 0.88 |
|  | #DIV/0! | 4.3E−04 | 5.1E−01 | 5.5E−04 | 4.1E−03 | 5.9E−02 |
| RR, 60-69 | 1.00 | 1.22 | 1.21 | 1.31 | 1.04 | 1.02 |
|  | #DIV/0! | 5.3E−03 | 5.3E−03 | 5.0E−03 | 7.7E−01 | 8.4E−01 |
| Secondary Progressive | 1.00 | 1.27 | 1.32 | 1.43 | 0.92 | 0.90 |
|  | #DIV/0! | 6.9E−04 | 1.5E−05 | 2.7E−05 | 5.2E−01 | 3.9E−01 |
| Primary Progressive | 1.00 | 1.13 | 1.25 | 1.14 | 0.91 | 0.91 |
|  | #DIV/0! | 1.7E−01 | 5.0E−03 | 2.5E−01 | 5.4E−01 | 5.2E−01 |
| Colon Cancer, All | 1.00 | 0.88 | 0.82 | 0.63 | 1.15 | 0.82 |
|  | #DIV/0! | 9.2E−05 | 1.2E−11 | 1.1E−23 | 3.2E−03 | 2.3E−05 |
| Ovarian Cancer | 1.00 | 0.81 | 0.80 | 0.67 | 0.96 | 0.75 |
|  | #DIV/0! | 2.2E−02 | 9.9E−03 | 2.3E−03 | 7.4E−01 | 4.2E−02 |
| Prostate Cancer | 1.00 | 0.79 | 0.79 | 0.66 | 0.97 | 0.87 |
|  | #DIV/0! | 5.0E−03 | 3.2E−03 | 4.3E−04 | 8.3E−01 | 2.5E−01 |
| Lung Cancer | 1.00 | 0.68 | 0.55 | 0.47 | 0.80 | 0.87 |
|  | #DIV/0! | 2.2E−05 | 1.4E−10 | 7.0E−08 | 9.6E−02 | 2.3E−01 |
| Renal Cancer | 1.00 | 0.88 | 0.68 | 0.81 | 0.39 | 0.36 |
|  | #DIV/0! | 7.5E−02 | 4.4E−07 | 3.0E−02 | 2.4E−08 | 4.0E−10 |
| Breast Cancer | 1.00 | 0.73 | 0.58 | 0.48 | 0.68 | 0.82 |
|  | #DIV/0! | 2.6E−04 | 1.6E−09 | 7.8E−08 | 6.5E−03 | 1.0E−01 |

Note:
AD stands for Alzheimer's Disease; and RR stands for Relapsing/Remitting Multiple Sclerosis.

TABLE 10

Table of serum changes (relative to controls) of plasmanyl GPEs, using diacyl 16:0/18:0 GPE as an internal standard.

|  | Plasmanyl GPEs | | | | | | | | | |
|---|---|---|---|---|---|---|---|---|---|---|
|  | 16:0/18:1 702.0/ 281.0 | 16:0/18:2 700.0/ 279.0 | 16:0/20:4 724.0/ 303.0 | 16:0/22:4 752.0/ 331.0 | 16:0/22:6 748.0/ 327.0 | 18:0/18:1 730.0/ 281.0 | 18:0/18:2 728.0/ 279.0 | 18:0/20:4 752.0/ 303.0 | 18:0/22:4 780.0/ 331.0 | 18:0/22:6 776.0/ 327.0 |
| AD, All | 0.84 | 0.83 | 0.62 | 0.66 | 0.63 | 0.91 | 0.82 | 0.71 | 0.79 | 0.80 |
|  | 5.6E−08 | 1.2E−06 | 4.7E−16 | 3.8E−13 | 1.5E−13 | 5.8E−05 | 8.0E−10 | 2.6E−20 | 8.1E−13 | 3.7E−07 |
| RR, All | 1.09 | 1.16 | 1.05 | 1.11 | 1.07 | 1.20 | 1.23 | 1.15 | 1.17 | 1.19 |
|  | 1.2E−03 | 7.0E−07 | 3.2E−01 | 1.3E−02 | 1.5E−01 | 2.5E−21 | 1.7E−16 | 8.7E−07 | 8.2E−10 | 1.2E−06 |

TABLE 10-continued

Table of serum changes (relative to controls) of plasmanyl GPEs, using diacyl 16:0/18:0 GPE as an internal standard.

| | \multicolumn{10}{c}{Plasmanyl GPEs} | | | | | | | | | |
|---|---|---|---|---|---|---|---|---|---|---|
| | 16:0/18:1 702.0/ 281.0 | 16:0/18:2 700.0/ 279.0 | 16:0/20:4 724.0/ 303.0 | 16:0/22:4 752.0/ 331.0 | 16:0/22:6 748.0/ 327.0 | 18:0/18:1 730.0/ 281.0 | 18:0/18:2 728.0/ 279.0 | 18:0/20:4 752.0/ 303.0 | 18:0/22:4 780.0/ 331.0 | 18:0/22:6 776.0/ 327.0 |
| RR, 20-29 | 0.88 | 1.02 | 0.84 | 0.75 | 0.87 | 1.04 | 1.21 | 0.98 | 0.92 | 1.15 |
| | 5.0E−01 | 9.1E−01 | 8.8E−02 | 4.2E−01 | 2.0E−01 | 3.0E−02 | 9.0E−03 | 5.6E−01 | 7.4E−01 | 5.4E−01 |
| RR, 30-39 | 0.91 | 0.88 | 0.79 | 0.84 | 1.01 | 1.13 | 0.95 | 0.98 | 1.03 | 1.23 |
| | 2.0E−01 | 1.9E−01 | 4.7E−02 | 9.2E−02 | 9.7E−01 | 2.4E−02 | 5.2E−01 | 8.4E−01 | 6.6E−01 | 8.2E−02 |
| RR, 40-49 | 1.05 | 1.12 | 1.05 | 0.99 | 1.09 | 1.13 | 1.19 | 1.16 | 1.11 | 1.25 |
| | 4.2E−01 | 6.9E−02 | 6.3E−01 | 9.3E−01 | 3.8E−01 | 2.2E−03 | 7.9E−04 | 1.8E−02 | 4.7E−02 | 9.0E−04 |
| RR, 50-59 | 1.03 | 1.07 | 0.91 | 1.01 | 0.95 | 1.16 | 1.17 | 1.04 | 1.07 | 1.10 |
| | 5.2E−01 | 1.5E−01 | 2.2E−01 | 8.7E−01 | 4.5E−01 | 1.8E−06 | 9.0E−05 | 4.2E−01 | 8.9E−02 | 8.5E−02 |
| RR, 60-69 | 1.09 | 1.28 | 1.13 | 1.16 | 1.29 | 1.20 | 1.27 | 1.23 | 1.28 | 1.52 |
| | 2.5E−01 | 6.0E−03 | 3.5E−01 | 2.2E−01 | 4.1E−02 | 8.6E−04 | 8.8E−04 | 9.9E−03 | 1.4E−03 | 4.7E−05 |
| Secondary Progressive | 1.22 | 1.29 | 1.40 | 1.28 | 1.67 | 1.25 | 1.27 | 1.28 | 1.28 | 1.68 |
| | 3.6E−03 | 2.1E−03 | 2.0E−03 | 2.5E−02 | 3.9E−06 | 5.9E−06 | 4.9E−04 | 5.8E−04 | 2.9E−04 | 4.6E−10 |
| Primary Progressive | 1.10 | 1.25 | 1.28 | 1.13 | 1.48 | 1.15 | 1.19 | 1.22 | 1.19 | 1.46 |
| | 2.8E−01 | 2.9E−01 | 7.2E−02 | 3.8E−01 | 4.3E−03 | 2.3E−02 | 4.4E−02 | 3.0E−02 | 4.6E−02 | 3.2E−04 |
| Colon Cancer, All | 0.70 | 0.53 | 0.58 | 0.55 | 0.61 | 0.78 | 0.55 | 0.69 | 0.76 | 0.86 |
| | 5.6E−24 | 1.1E−39 | 2.4E−18 | 1.6E−22 | 1.2E−15 | 5.8E−25 | 3.3E−51 | 3.8E−24 | 1.9E−16 | 1.4E−04 |
| Ovarian Cancer | 0.74 | 0.61 | 0.57 | 0.53 | 0.63 | 0.85 | 0.65 | 0.68 | 0.70 | 1.00 |
| | 1.3E−03 | 1.7E−04 | 1.9E−03 | 6.1E−04 | 1.1E−02 | 1.1E−02 | 3.2E−05 | 3.2E−04 | 3.4E−04 | 9.9E−01 |
| Prostate Cancer | 0.75 | 0.68 | 0.53 | 0.67 | 0.62 | 0.85 | 0.73 | 0.71 | 0.87 | 0.80 |
| | 6.5E−04 | 6.0E−04 | 1.3E−04 | 6.2E−03 | 3.5E−03 | 4.6E−03 | 4.0E−04 | 2.6E−04 | 7.7E−02 | 4.3E−02 |
| Lung Cancer | 0.45 | 0.37 | 0.24 | 0.24 | 0.20 | 0.60 | 0.47 | 0.44 | 0.51 | 0.37 |
| | 1.2E−13 | 9.0E−12 | 1.1E−09 | 5.1E−10 | 1.2E−09 | 1.4E−13 | 2.2E−12 | 6.3E−12 | 1.1E−10 | 6.6E−10 |
| Renal Cancer | 0.68 | 0.56 | 0.42 | 0.53 | 0.49 | 0.76 | 0.61 | 0.54 | 0.63 | 0.74 |
| | 1.2E−06 | 1.3E−07 | 2.8E−07 | 2.3E−05 | 2.0E−05 | 7.6E−07 | 1.6E−08 | 5.9E−10 | 1.0E−07 | 4.6E−03 |
| Breast Cancer | 0.54 | 0.43 | 0.29 | 0.33 | 0.27 | 0.72 | 0.51 | 0.51 | 0.64 | 0.41 |
| | 4.7E−10 | 6.2E−10 | 1.2E−08 | 4.9E−08 | 2.6E−08 | 1.6E−07 | 1.5E−10 | 7.8E−10 | 1.5E−06 | 8.0E−09 |

Note:
AD stands for Alzheimer's Disease; and RR stands for Relapsing/Remitting Multiple Sclerosis.

TABLE 11

Table of serum changes (relative to controls) of plasmenyl GPEs, using diacyl 16:0/18:0 GPE as an internal standard.

| | \multicolumn{10}{c}{Plasmenyl GPEs} | | | | | | | | | |
|---|---|---|---|---|---|---|---|---|---|---|
| | 16:0/18:1 700.0/ 281.0 | 16:0/18:2 698.0/ 279.0 | 16:0/20:4 722.0/ 303.0 | 16:0/22:4 750.0/ 331.0 | 16:0/22:6 746.0/ 327.0 | 18:0/18:1 728.0/ 281.0 | 18:0/18:2 726.0/ 279.0 | 18:0/20:4 750.6/ 303.2 | 18:0/22:4 778.0/ 331.0 | 18:0/22:6 774.0/ 327.0 |
| AD, All | 0.79 | 0.76 | 0.63 | 0.65 | 0.67 | 0.83 | 0.78 | 0.73 | 0.71 | 0.76 |
| | 2.9E−16 | 1.1E−11 | 3.5E−15 | 2.5E−16 | 6.0E−11 | 1.1E−07 | 7.0E−09 | 2.5E−09 | 2.1E−15 | 1.8E−06 |
| RR, All | 1.12 | 1.17 | 1.08 | 1.12 | 1.09 | 1.12 | 1.18 | 1.10 | 1.10 | 1.12 |
| | 8.5E−07 | 1.3E−07 | 1.2E−01 | 3.1E−03 | 7.0E−02 | 1.3E−04 | 3.3E−07 | 3.0E−02 | 3.5E−03 | 1.4E−02 |
| RR, 20-29 | 0.94 | 1.00 | 0.75 | 0.74 | 0.85 | 0.84 | 0.99 | 0.79 | 0.82 | 0.80 |
| | 7.0E−01 | 9.1E−01 | 6.0E−02 | 3.8E−01 | 1.7E−01 | 2.1E−01 | 7.3E−01 | 4.7E−02 | 3.0E−01 | 6.3E−02 |
| RR, 30-39 | 0.95 | 0.88 | 0.85 | 0.89 | 1.04 | 0.89 | 1.07 | 0.87 | 0.88 | 1.07 |
| | 3.9E−01 | 1.9E−01 | 2.3E−01 | 2.4E−01 | 7.9E−01 | 1.7E−01 | 2.1E−01 | 3.2E−01 | 1.6E−01 | 6.8E−01 |
| RR, 40-49 | 1.10 | 1.18 | 1.12 | 1.03 | 1.18 | 1.09 | 1.14 | 1.13 | 1.04 | 1.17 |
| | 5.3E−02 | 7.1E−03 | 2.7E−01 | 7.1E−01 | 8.3E−02 | 1.5E−01 | 4.9E−02 | 1.8E−01 | 5.7E−01 | 9.4E−02 |
| RR, 50-59 | 1.07 | 1.09 | 0.96 | 1.02 | 0.98 | 1.08 | 1.11 | 0.98 | 1.00 | 1.02 |
| | 7.6E−02 | 7.4E−02 | 6.2E−01 | 7.6E−01 | 7.7E−01 | 1.0E−01 | 4.1E−02 | 8.0E−01 | 1.0E+00 | 7.6E−01 |
| RR, 60-69 | 1.17 | 1.26 | 1.17 | 1.22 | 1.33 | 1.21 | 1.31 | 1.24 | 1.20 | 1.44 |
| | 1.2E−02 | 6.5E−03 | 2.1E−01 | 8.1E−02 | 2.4E−02 | 1.3E−02 | 3.2E−03 | 5.2E−02 | 8.6E−02 | 1.8E−03 |
| Secondary Progressive | 1.10 | 1.21 | 1.33 | 1.41 | 1.63 | 1.27 | 1.42 | 1.35 | 1.71 | |
| | 1.2E−01 | 2.2E−02 | 9.3E−03 | 2.7E−04 | 6.8E−06 | 9.8E−03 | 6.9E−03 | 4.5E−04 | 2.9E−04 | 3.4E−07 |
| Primary Progressive | 1.08 | 1.19 | 1.29 | 1.15 | 1.51 | 1.18 | 1.28 | 1.36 | 1.20 | 1.70 |
| | 3.2E−01 | 9.2E−02 | 6.0E−02 | 2.7E−01 | 2.2E−03 | 7.7E−02 | 2.5E−02 | 1.3E−02 | 8.5E−02 | 3.6E−05 |
| Colon Cancer, All | 0.84 | 0.55 | 0.55 | 0.57 | 0.68 | 0.72 | 0.49 | 0.53 | 0.61 | 0.67 |
| | 3.8E−10 | 3.3E−38 | 1.7E−22 | 1.6E−24 | 1.8E−11 | 1.6E−18 | 4.7E−42 | 2.0E−27 | 3.5E−27 | 5.6E−12 |
| Ovarian Cancer | 0.80 | 0.60 | 0.62 | 0.59 | 0.74 | 0.74 | 0.58 | 0.63 | 0.61 | 0.77 |
| | 4.4E−03 | 5.1E−05 | 5.4E−03 | 8.4E−04 | 7.1E−02 | 3.1E−03 | 9.1E−05 | 3.7E−03 | 1.6E−04 | 1.2E−01 |
| Prostate Cancer | 0.78 | 0.66 | 0.54 | 0.69 | 0.72 | 0.70 | 0.65 | 0.58 | 0.75 | 0.70 |
| | 6.2E−04 | 1.4E−04 | 1.2E−04 | 4.8E−03 | 3.2E−02 | 1.5E−04 | 6.6E−05 | 2.3E−04 | 6.9E−03 | 2.0E−02 |
| Lung Cancer | 0.61 | 0.50 | 0.29 | 0.29 | 0.27 | 0.47 | 0.41 | 0.33 | 0.39 | 0.29 |
| | 1.1E−09 | 1.3E−08 | 3.9E−09 | 7.7E−11 | 2.0E−08 | 3.8E−11 | 1.0E−09 | 5.8E−09 | 4.2E−11 | 4.2E−08 |
| Renal Cancer | 0.65 | 0.52 | 0.44 | 0.53 | 0.55 | 0.61 | 0.48 | 0.48 | 0.54 | 0.56 |
| | 1.2E−09 | 3.7E−09 | 4.0E−07 | 2.8E−06 | 1.4E−04 | 8.4E−08 | 2.6E−09 | 7.1E−07 | 5.2E−08 | 2.2E−04 |

TABLE 11-continued

Table of serum changes (relative to controls) of plasmenyl GPEs, using diacyl 16:0/18:0 GPE as an internal standard.

| | Plasmenyl GPEs | | | | | | | | | |
|---|---|---|---|---|---|---|---|---|---|---|
| | 16:0/18:1 700.0/ 281.0 | 16:0/18:2 698.0/ 279.0 | 16:0/20:4 722.0/ 303.0 | 16:0/22:4 750.0/ 331.0 | 16:0/22:6 746.0/ 327.0 | 18:0/18:1 728.0/ 281.0 | 18:0/18:2 726.0/ 279.0 | 18:0/20:4 750.6/ 303.2 | 18:0/22:4 778.0/ 331.0 | 18:0/22:6 774.0/ 327.0 |
| Breast Cancer | 0.62 2.3E−09 | 0.46 1.1E−09 | 0.31 1.0E−08 | 0.36 5.0E−09 | 0.30 7.1E−08 | 0.53 3.7E−09 | 0.43 2.2E−09 | 0.35 1.4E−08 | 0.46 4.5E−09 | 0.32 1.3E−07 |

Note:
AD stands for Alzheimer's Disease; and RR stands for Relapsing/Remitting Multiple Sclerosis.

REFERENCES

1. Nagan N, Zoeller R A. Plasmalogens: biosynthesis and functions. Prog Lipid Res 2001; 40(3):199-229.
2. de Duve D. The peroxisome: a new cytoplasmic organelle. Proceedings of the Royal Society of London Series B, Containing papers of a Biological character 1969; 173 (30):71-83.
3. van den Bosch H, Schutgens R B, Wanders R J, Tager J M. Biochemistry of peroxisomes. Annu Rev Biochem 1992; 61:157-97.
4. Bowen P, Lee C S, Zellweger H, Lindenberg R. A Familial Syndrome of Multiple Congenital Defects. Bulletin of the Johns Hopkins Hospital 1964; 114:402-14.
5. Goldfischer S, Moore C L, Johnson A B, et al. Peroxisomal and mitochondrial defects in the cerebro-hepato-renal syndrome. Science 1973; 182(107):62-4.
6. Wanders R J. Peroxisomal disorders: clinical, biochemical, and molecular aspects. Neurochem Res 1999; 24(4): 565-80.
7. Alkan A, Kutlu R, Yakinci C, Sigirci A, Aslan M, Sarac K. Delayed myelination in a rhizomelic chondrodysplasia punctata case: MR spectroscopy findings. Magnetic resonance imaging 2003; 21(1):77-80.
8. Sztriha L, Al-Gazali L I, Wanders R J, Ofman R, Nork M, Lestringant G G. Abnormal myelin formation in rhizomelic chondrodysplasia punctata type 2 (DHAPAT-deficiency). Developmental medicine and child neurology 2000; 42(7):492-5.
9. Behl P, Lanctot K L, Streiner D L, Guimont I, Black S E. Cholinesterase inhibitors slow decline in executive functions, rather than memory, in Alzheimer's disease: a 1-year observational study in the Sunnybrook dementia cohort. Current Alzheimer research 2006; 3(2):147-56.
10. Sparks D L, Sabbagh M, Connor D, et al. Statin therapy in Alzheimer's disease. Acta Neurol Scand Suppl 2006; 185:78-86.
11. Perichon R, Moser A B, Wallace W C, Cunningham S C, Roth G S, Moser H W. Peroxisomal disease cell lines with cellular plasmalogen deficiency have impaired muscarinic cholinergic signal transduction activity and amyloid precursor protein secretion. Biochem Biophys Res Commun 1998; 248(1):57-61.
12. Artaz M A, Boddaert J, Heriche-Taillandier E, Dieudonne B, Verny M. [Medical comorbidity in Alzheimer's disease: baseline characteristics of the REAL.FR Cohort]. La Revue de medecine interne/fondee 2006; 27(2):91-7.
13. Amieva H, Jacqmin-Gadda H, Orgogozo J M, et al. The 9 year cognitive decline before dementia of the Alzheimer type: a prospective population-based study. Brain 2005; 128(Pt 5):1093-101.
14. Esiri M M, Biddolph S C, Morris C S. Prevalence of Alzheimer plaques in AIDS. J Neurol Neurosurg Psychiatry 1998; 65(1):29-33.

What is claimed is:

1. A method to detect or monitor, and treat adult onset plasmalogen biosynthesis disorder in a living subject older than forty years of age, comprising the steps of:
   a) performing a mass spectrometry assay on at least one blood sample from said subject prior to, during, or following administration of an age-related plasmalogen deficiency-targeted therapy to the subject, using a Fourier transform ion cyclotron resonance, time of flight, orbitrap, quadrupole or triple quadrupole mass spectrometer to obtain quantifying data for one or more than one metabolite marker selected from plasmanyl glycerylphosphoethanolamines to measure the level of said one or more than one metabolite marker in said at least one blood sample;
   b) generating a result of said mass spectrometry assay, said result comprising at least the presence of a decrease in the level of said one or more than one metabolite marker in said at least one blood sample based on a comparison of said quantifying data for said one or more than one metabolite marker to corresponding data obtained from one or more than one reference sample;
   c) assigning the subject as having adult onset plasmalogen biosynthesis disorder based on the decrease in the level of said one or more than one metabolite marker in said at least one blood sample from the subject; and
   d) administering to the subject assigned as having adult onset plasmalogen biosynthesis disorder an age-related plasmalogen deficiency-targeted therapy.

2. The method according to claim 1, further comprising:
   performing a mass spectrometry assay on at least one blood sample from said subject using a Fourier transform ion cyclotron resonance, time of flight, orbitrap, quadrupole or triple quadrupole mass spectrometer to obtain quantifying data for one or more than one internal control metabolite; and
   generating a ratio for each of the levels of said one or more than one metabolite marker to the level obtained for the one or more than one internal control metabolite;
   wherein step (b) comprises comparing each ratio to one or more corresponding ratios obtained for the one or more than one reference sample.

3. The method according to claim 2, wherein the one or more than one internal control metabolite is a diacyl glycerophosphoethanolamine (PtdEt).

4. The method according to claim 3, wherein the diacyl glycerophosphoethanolamine is PtdEt 16:0/18:0.

5. The method according to claim 4, wherein the mass spectrometry assay carried out on the one or more than one internal control metabolite is carried out by MS/MS transition and the MS/MS transition for the PtdEt 16:0/18:0 is 718.0/255.0.

6. The method according to claim 1, wherein the plasmanyl glycerylphosphoethanolamines are selected from the group consisting of: plasmanyl 16:0/18:1, plasmanyl 16:0/18:2, plasmanyl 16:0/20:4, plasmanyl 16:0/22:4, plasmanyl 16:0/22:6, plasmanyl 18:0/18:1, plasmanyl 18:0/18:2, plasmanyl 18:0/20:4, plasmanyl 18:0/22:4, plasmanyl 18:0/22:6, and combinations thereof.

7. The method according claim 6, wherein the mass spectrometry assay is carried out by MS/MS transition and the MS/MS transitions for the plasmanyl glycerylphosphoethanolamines are: 702.0/281.0, 700.0/279.0, 724.0/303.0, 752.0/331.0, 748.0/327.0, 730.0/281.0, 728.0/279.0, 752.0/303.0, 780.0/331.0 and 776.0/327.0, respectively.

8. The method according to claim 1, further comprising monitoring of the subject for a change in or risk of a plasmalogen deficiency-related human health disorder in said subject.

9. The method according to claim 1, wherein the mass spectrometry assay is carried out using a Fourier transform ion cyclotron resonance mass spectrometer.

10. The method according to claim 9, wherein the mass spectrometer is equipped with a chromatographic system.

11. The method according to claim 1, wherein the at least one blood sample is a blood serum sample.

12. The method according to claim 1, wherein said performing comprises:
conducting a liquid/liquid extraction on the at least one blood sample whereby non-polar metabolites are dissolved in an organic solvent and polar metabolites are dissolved in an aqueous solvent.

13. The method according to claim 12, wherein the mass spectrometry assay is carried out using electrospray ionization or atmospheric pressure chemical ionization to afford ionization products of said one or more than one metabolite marker.

14. The method according to claim 12, wherein the mass spectrometry assay is carried out using MS/MS transition.

15. The method according to claim 12, wherein the mass spectrometry assay is carried out by chromatography and MS/MS transition.

16. The method according to claim 1, wherein said adult onset plasmalogen biosynthesis disorder is not caused by a peroxisomal biogenesis disorder.

17. A method to detect or monitor, and treat adult onset plasmalogen biosynthesis disorder in a living subject older than forty years of age, comprising the steps of:
a) introducing a blood sample obtained from said subject prior to, during, or following administration of an age-related plasmalogen deficiency-targeted therapy to said subject into a Fourier transform ion cyclotron resonance, time of flight, orbitrap, quadrupole or triple quadrupole mass spectrometer to cause ionization of one or more than one metabolite marker selected from plasmanyl glycerylphosphoethanolamines and thereby form ionization products of said one or more than one metabolite marker,
b) measuring the amount of ionization products of said one or more than one metabolite marker using the mass spectrometer and, based on the measured amount of ionization products, obtaining quantifying data for said one or more than one metabolite marker in said blood sample;
c) identifying the presence of a decrease in the level of said one or more than one metabolite marker in said blood sample based on a comparison of said quantifying data for said one or more than one metabolite marker to corresponding quantifying data obtained from one or more than one reference sample;
d) assigning the subject as having adult onset plasmalogen biosynthesis disorder based on the decrease in the level of said one or more than one metabolite marker in said blood sample from the subject; and
e) administering to the subject assigned as having adult onset plasmalogen biosynthesis disorder an age-related plasmalogen deficiency-targeted therapy.

18. The method according to claim 17, wherein said measuring is carried out by multiple reaction monitoring for one parent/daughter transition for said one or more than one metabolite marker.

19. The method according to claim 17, wherein the sample introduced into the mass spectrometer is a product of liquid/liquid extraction performed on a blood sample from the subject, whereby during the liquid/liquid extraction non-polar metabolites are dissolved in an organic solvent and polar metabolites are dissolved in an aqueous solvent.

* * * * *